US011364269B2

(12) United States Patent
Becattini et al.

(10) Patent No.: US 11,364,269 B2
(45) Date of Patent: Jun. 21, 2022

(54) **METHODS AND COMPOSITIONS FOR REDUCING *LISTERIA MONOCYTOGENES* INFECTION OR COLONIZATION**

(71) Applicant: MEMORIAL SLOAN-KETTERING CANCER CENTER, New York, NY (US)

(72) Inventors: Simone Becattini, New York, NY (US); Eric Pamer, Montclair, NJ (US); Sohn Kim, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/688,632

(22) Filed: Nov. 19, 2019

(65) Prior Publication Data

US 2020/0085886 A1     Mar. 19, 2020

Related U.S. Application Data

(63) Continuation of application No. PCT/US2018/032694, filed on May 15, 2018.

(60) Provisional application No. 62/508,547, filed on May 19, 2017.

(51) Int. Cl.
*A61K 35/742* (2015.01)
*A61P 31/04* (2006.01)
*A61K 9/00* (2006.01)

(52) U.S. Cl.
CPC .......... *A61K 35/742* (2013.01); *A61K 9/0031* (2013.01); *A61K 9/0056* (2013.01); *A61P 31/04* (2018.01)

(58) Field of Classification Search
CPC .... A61K 35/742; A61K 35/74; A61K 9/0056; A61K 9/0031; C12R 1/01; C12R 2001/145; C12N 1/20; A61P 31/04
See application file for complete search history.

(56) References Cited

U.S. PATENT DOCUMENTS

| 2013/0202571 A1* | 8/2013 | Bhunia ............... A61K 35/747 424/93.45 |
| 2016/0040215 A1 | 2/2016 | Henn et al. |
| 2016/0158295 A1* | 6/2016 | Afeyan ............... A61K 35/741 424/464 |
| 2016/0193257 A1 | 7/2016 | Honda et al. |
| 2016/0199424 A1 | 7/2016 | Berry et al. |
| 2017/0290889 A1* | 10/2017 | Loke ..................... C07K 14/54 |

FOREIGN PATENT DOCUMENTS

| WO | WO-2014121304 A1 * | 8/2014 | ............ C12N 1/20 |
| WO | WO 2015/077794 A1 | 5/2015 | |

OTHER PUBLICATIONS

Forrester, J. D. et al. 2014. Clostridium ramosum Bacteremia: Case Report and Literature Review. Surgical infections. 15(3): 343-346. (Year: 2014).*
Mahondas, R. et al. 2001. Clostridium ramosum Bacteremia and Osteomyelitis in a Patient with Infected Pressure Sores. Infectious Disease in Clinical Practice. 10(2): 123-124. (Year: 2001).*
Elsayed, S. et al. 2004. Human Infection Caused by Clostridium hathewayi. Emerging Infectious Diseases. 10(11): 1950-1952. (Year: 2004).*
Abt et al., "Innate Immune Defenses Mediated by Two ILC Subsets are Critical for Protection Against Acute *Clostridium difficile* Infection", Cell Host Microbe, 18(1):27-37 (2015).
Atarashi et al., "$T_{reg}$ induction by a rationally selected mixture of Clostridia strains from the human microbiota", Nature, 500:232-236 (2013).
Becattini et al., "Abstract A082: Identification of commensal bacterial strains that provide resistance to *L. monocytogenes* infection," Cancer Immunology Research, 4(11), Abstract only (2016).
Becattini et al., "Commensal microbes provide first line defense against *Listeria monocytogenes* infection," The Journal of Experimental Medicine, 214(7):1973-1989 (2017).
Buffie et al., "Precision microbiome reconstitution restores bile acid mediated resistance to *Clostridium difficile*", Nature, 517:205-208 (2015).
Caporaso et al., "Ultra-high-throughput microbial community analysis on the Illumina HiSeq and MiSeq platforms", The ISME Journal, 6:1621-1624 (2012).
DeSantis et al., "Greengenes, a Chimera-Checked 16S rRNA Gene Database and Workbench Compatible with ARB", Applied and Environmental Microbiology, 72(7):5069-5072 (2006).
Edgar et al., "Error filtering, pair assembly and error correction for next-generation sequencing reads", Bioinformatics, 31(21):1-7 (2015).
Edgar, "UPARSE: highly accurate OTU sequences from microbial amplicon reads", Nature Methods, 10(10):996-998 (2013).
International Search Report and Written Opinion dated Aug. 23, 2018 in International Application No. PCT/US2018/032694.
Remington's Pharmaceutical Sciences, 18$^{th}$ ed. A.R. Gennaro, ed. Mack Publishing Company, Easton, PA (1980).
Schloss et al., "Introducing mothur: Open-Source, Platform-Independent, Community-Supported Software for Describing and Comparing Microbial Communities", Applied and Environmental Microbiology, 75(23):7537-7541 (2009).

(Continued)

*Primary Examiner* — Ruth A Davis
(74) *Attorney, Agent, or Firm* — Baker Botts L.L.P.

(57) ABSTRACT

The disclosure relates to a therapeutic composition for treating *L. monocytogenes* infection or *L. monocytogenes* colonization, the composition including at least one, at least two, at least three, or all of an isolated *C. saccharogumia* bacteria, an isolated *C. ramosum* bacteria, an isolated *C. hathewayi* bacteria, and/or an isolated *B. producta* bacteria in a formulation suitable for administration to a subject. The disclosure further provides similar compositions lacking an isolated *C. saccharogumia* bacteria. The disclosure additionally provides methods of treating *L. monocytogenes* infection or colonization using such compositions.

12 Claims, 22 Drawing Sheets
Specification includes a Sequence Listing.

(56) References Cited

OTHER PUBLICATIONS

Ubeda et al., "Familial Transmission rather than defective innate immunity shapes the distinct intestinal microbiota of TLR-deficient mice", The Journal of Experimental Medicine, 209(8):1445-1456 (2012).

Ubeda et al., "Intestinal Microbiota Containing *Barnesiella* Species Cures Vancomycin-Resistant *Enterococcus faecium* Colonization", Infection and Immunity, 81(3):965-973 (2013).

Viaud et al., "The intestinal microbiota modulates the anticancer immune effects of cyclophosphamide", Science, 342(6161):971-976 (2013).

European Search Report dated Mar. 12, 2021 in Application No. EP 18802196.

\* cited by examiner

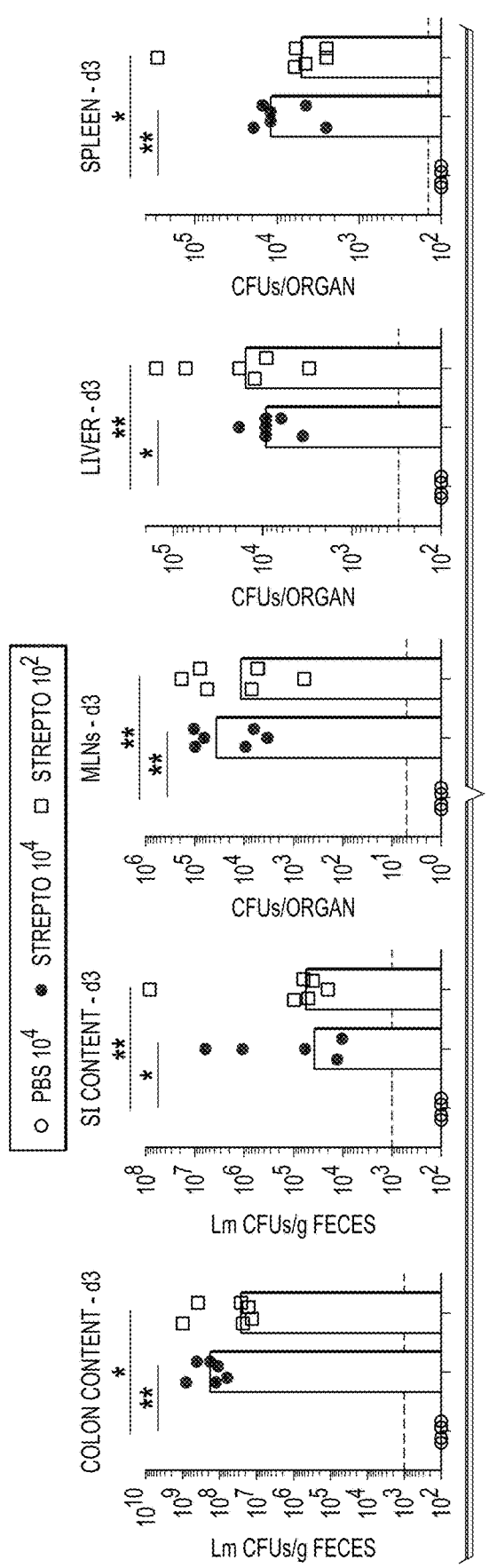
FIG. 5C
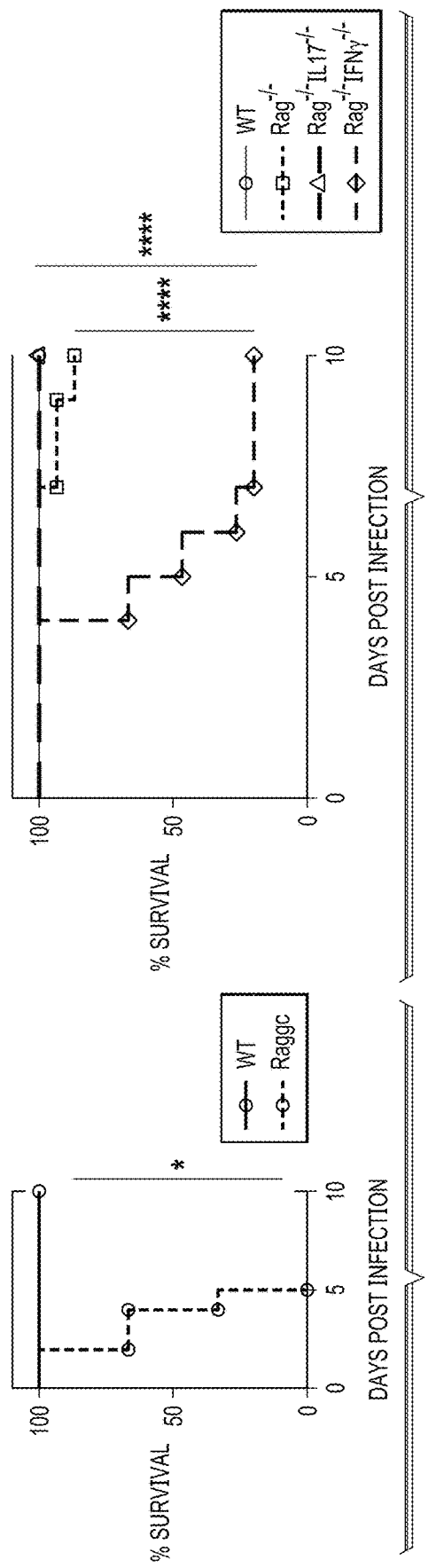
FIG. 6A
FIG. 6B

METHODS AND COMPOSITIONS FOR REDUCING *LISTERIA MONOCYTOGENES* INFECTION OR COLONIZATION

PRIORITY CLAIM

The present application is a continuation of and claims priority to International Patent Application No. PCT/US2018/032694, filed May 15, 2018, which claims priority to U.S. Provisional Patent Application Ser. No. 62/508,547, filed May 19, 2017 and titled "METHODS AND COMPOSITIONS FOR REDUCING *LISTERIA MONOCYTOGENES* INFECTION OR COLONIZATION," which are incorporated by reference herein in their entireties.

GRANT INFORMATION

This invention was made with government support under AI039031 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 19, 2019, is named 072734_0983 SL.txt and is 1,336 bytes in size.

TECHNICAL FIELD

The present invention relates to compositions and methods for decreasing the risk of developing *Listeria monocytogenes* infection or colonization and for treating *L. monocytogenes* infection or colonization.

BACKGROUND

*L. monocytogenes* is a Gram positive, facultative intracellular bacterium that can contaminate food which, upon ingestion, can result in infection of a wide range of animals, including livestock and humans. The severity and extent of *L. monocytogenes* infection is determined by the virulence of the bacterial strain and the host's immune status. Ingestion of *L. monocytogenes* contaminated food by immune competent individuals is often limited to gastroenteritis that resolves in a few days, with clearance of the pathogen from the intestine.

Pregnant women, infants, older adults and immunocompromised individuals, in particular cancer patients, are at risk for systemic *L. monocytogenes* infections. The remarkable capacity of *L. monocytogenes* to infect the placenta can result in septic abortion and neonatal infection, while in immunocompromised adults bacteremia and meningo-encephalitis are the major syndromes associated with *L. monocytogenes* infection. Patients with cancer have some of the highest incidences of systemic *L. monocytogenes* infection, and, while cell-mediated immune function may be compromised in these patients, predisposing factors in humans to *L. monocytogenes* infection remain incompletely defined.

*L. monocytogenes* outbreaks are associated with food contamination, however most listeriosis cases that occur in immunocompromised hosts are sporadic and likely result from ingestion of low numbers of bacteria that are known to contaminate many foods meant to be cooked prior to ingestion. In the general population, exposure to *L. monocytogenes* and asymptomatic clearance are believed to occur several times per year.

*L. monocytogenes* has been studied extensively over the past century and has become one of the most widely utilized model pathogens in experimental immunology. *L. monocytogenes* studies have generally involved intravenous inoculation, a convenient and reproducible model to dissect systemic infection and immune response mechanisms. Intravenous delivery, however, bypasses the intestinal phase of *L. monocytogenes* infection, which otherwise precedes systemic spread and has an important role in the overall pathogenesis of infection. As a consequence, many aspects of the intestinal phase of *L. monocytogenes* infection remain obscure.

Even though ingestion of *L. monocytogenes* from contaminated food is the main cause of infection in humans, there is little clinical information on the early intestinal stages of *L. monocytogenes* infection that might enhance resistance, and preventive interventions target the contaminated food itself.

Previous studies have suggested, although never conclusively proven, that gut commensals can protect the host from *L. monocytogenes* infection. Nor have these studies identified the responsible commensal bacteria. It was previously reported that germ free (GF) mice, in contrast to specific pathogen free (SPF) mice, were highly susceptible to *L. monocytogenes* infection, and their colon would become rapidly colonized by *L. monocytogenes* following low intragastric inocula. It was hypothesized that the rich microbiota carried by SPF mice might account for their resistance to infection, but gavage of selected bacterial species was unable to prevent intestinal growth of *L. monocytogenes*, even though this treatment reduced penetration of *L. monocytogenes* into intestinal tissue, as assessed by microscopy. Similarly, it was previously observed that GF rats, in contrast to conventional rats, were highly permissive for *L. monocytogenes* expansion in the intestine, and that intestinal clearance of *L. monocytogenes* could be achieved in these animals by transplantation of a microbiota, but specific bacteria were not identified.

Susceptibility to *L. monocytogenes* infection in mice following antibiotic administration is exacerbated by concurrent corticosteroid administration, suggesting that the immune system and the gut microbiota make distinct contributions to the control of *L. monocytogenes* infection. In addition, it has been demonstrated that cross-transfer of microbiota from C57Bl/6 mice and BALB/c mice did not increase the susceptibility to *Listeria* infection in the former strain, nor reduced it in the latter. As both strains likely harbor microbiota with similar complexity and protective activity, genetic and immune factors are likely responsible for the outcome of infection when colonization resistance is intact.

Finally, the ability of the microbiota to cure patients with recurrent *Clostridium difficile* infections has been demonstrated in a randomized, controlled trial of fecal microbiota transplantation (FMT), but FMT has not been tested as treatment for listeriosis.

SUMMARY

The disclosure provides a therapeutic composition for treating *L. monocytogenes* infection or *L. monocytogenes* colonization, the composition including at least one or at least two of an isolated *Clostridium saccharogumia* (*C. saccharogumia*) bacteria, an isolated *Clostridium ramosum*

(*C. ramosum*) bacteria, an isolated *Clostridium hathewayi* (*C. hathewayi*) bacteria, and/or an isolated *Blautia producta* (*B. producta*) bacteria in a formulation suitable for administration to a subject.

The disclosure further provides the following additional embodiments, all of which may be combined with the above composition and with one another, unless clearly mutually exclusive: i) the composition may include at least three of an isolated *C. saccharogumia* bacteria, an isolated *C. ramosum* bacteria, an isolated *C. hathewayi* bacteria, and/or an isolated *B. producta* bacteria; ii) the composition may include an isolated *C. saccharogumia* bacteria, an isolated *C. ramosum* bacteria, an isolated *C. hathewayi* bacteria, and an isolated *B. producta* bacteria; iii) the composition may include at least one or at least two of an isolated *C. ramosum* bacteria, an isolated *C. hathewayi* bacteria, and/or an isolated *B. producta* bacteria; iv) the composition may include an isolated *C. ramosum* bacteria, an isolated *C. hathewayi* bacteria, and an isolated *B. producta* bacteria; v) at least one isolated bacteria may be an isolated viable bacteria; vi) at least one isolated bacteria may be an isolated spore thereof; vii) the composition may be formulated for oral, nasogastric, or rectal administration; viii) the composition may be a liquid, suspension, dried powder, tablet, capsule or food product; ix) the composition may include at least $10^5$ bacteria of each isolated bacteria The disclosure further provides a method for reducing the risk of *L. monocytogenes* infection or *L. monocytogenes* colonization in a subject, and/or increasing resistance to *L. monocytogenes* infection or *L. monocytogenes* colonization in the subject, and/or reducing the severity of *L. monocytogenes* infection in the subject, and/or reducing the amount of *L. monocytogenes* colonizing the subject, including administering, to the subject in need of such treatment, a therapeutically effective amount of a composition including at least two of a *C. saccharogumia* bacteria, a *C. ramosum* bacteria, a *C. hathewayi* bacteria, and/or a *B. producta* bacteria in a formulation suitable for administration to the subject.

The disclosure further provides the following additional embodiments, all of which may be combined with the above composition and with one another, unless clearly mutually exclusive: i) the method in which the composition is any composition described above or herein; ii) the method in which the composition includes at least one, two, or three of three of a *C. saccharogumia* bacteria, a *C. ramosum* bacteria, a *C. hathewayi* bacteria, and/or a *B. producta* bacteria; iii) the method in which the composition includes a *C. saccharogumia* bacteria, a *C. ramosum* bacteria, a *C. hathewayi* bacteria, and a *B. producta* bacteria; iv) the method in which the composition includes at least one or at least two of a *C. ramosum* bacteria, a *C. hathewayi* bacteria, and/or a *B. producta* bacteria; v) the method in which the composition includes a *C. ramosum* bacteria, a *C. hathewayi* bacteria, and a *B. producta* bacteria; vi) the method, further including reducing the risk of invasive listeriosis in the subject; vii) the method further including reducing the risk of miscarriage, stillbirth, or premature labor in a pregnant subject; viii) the method further including administering at least $10^5$ bacteria of each bacteria administered; ix) the method including administering at least one bacteria as an isolated viable bacteria; x) the method including administering at least one bacteria as an isolated spore thereof; xi) the method in which the composition formulated for oral, nasogastric, or rectal administration, x) the method in which the composition is a liquid, suspension, dried powder, tablet, capsule or food product; xi) the method in which the therapeutically effective amount ameliorates at least one symptom of *L. monocytogenes* infection selected from the group consisting of abdominal tenderness, abdominal pain, abdominal cramping, diarrhea, nausea, vomiting, fever, chills, fatigue, muscle aches, headache, stiff neck, back ache, confusion, loss of balance, convulsions, sepsis, meningitis, chorioamnionitis, meningo-encephalitis, and/or death, and, in pregnant subjects, placental infection, miscarriage, stillbirth, and/or premature labor; xii) the method in which the therapeutically effective amount inhibits proliferation of *L. monocytogenes* in the gastrointestinal tract of the subject; xiii) the method in which the therapeutically effective amount inhibits proliferation of *L. monocytogenes* in the large intestine of the subject; xiv) the method also including evaluating the *L. monocytogenes* infection or *L. monocytogenes* colonization in the subject by culturing a sample from the subject; xv) the method also includes evaluating the *L. monocytogenes* infection or *L. monocytogenes* colonization in the subject by detecting a *L. monocytogenes* biomarker in a sample from the subject; xv) the method also includes administering the therapeutic composition before, during or after antibiotic therapy;

xvi) the method also includes administering the therapeutic composition before, during, or after chemotherapy.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which:

FIG. 5C is a set of graphs of *L. monocytogenes* burden in various organs of the mice;

FIG. 6A is a graph of survival of immunocompromised mice infected with *L. monocytogenes*;

FIG. 6B is a graph of survival of various types of immunocompromised mice infected with *L. monocytogenes*;

DETAILED DESCRIPTION

Figure 1A:
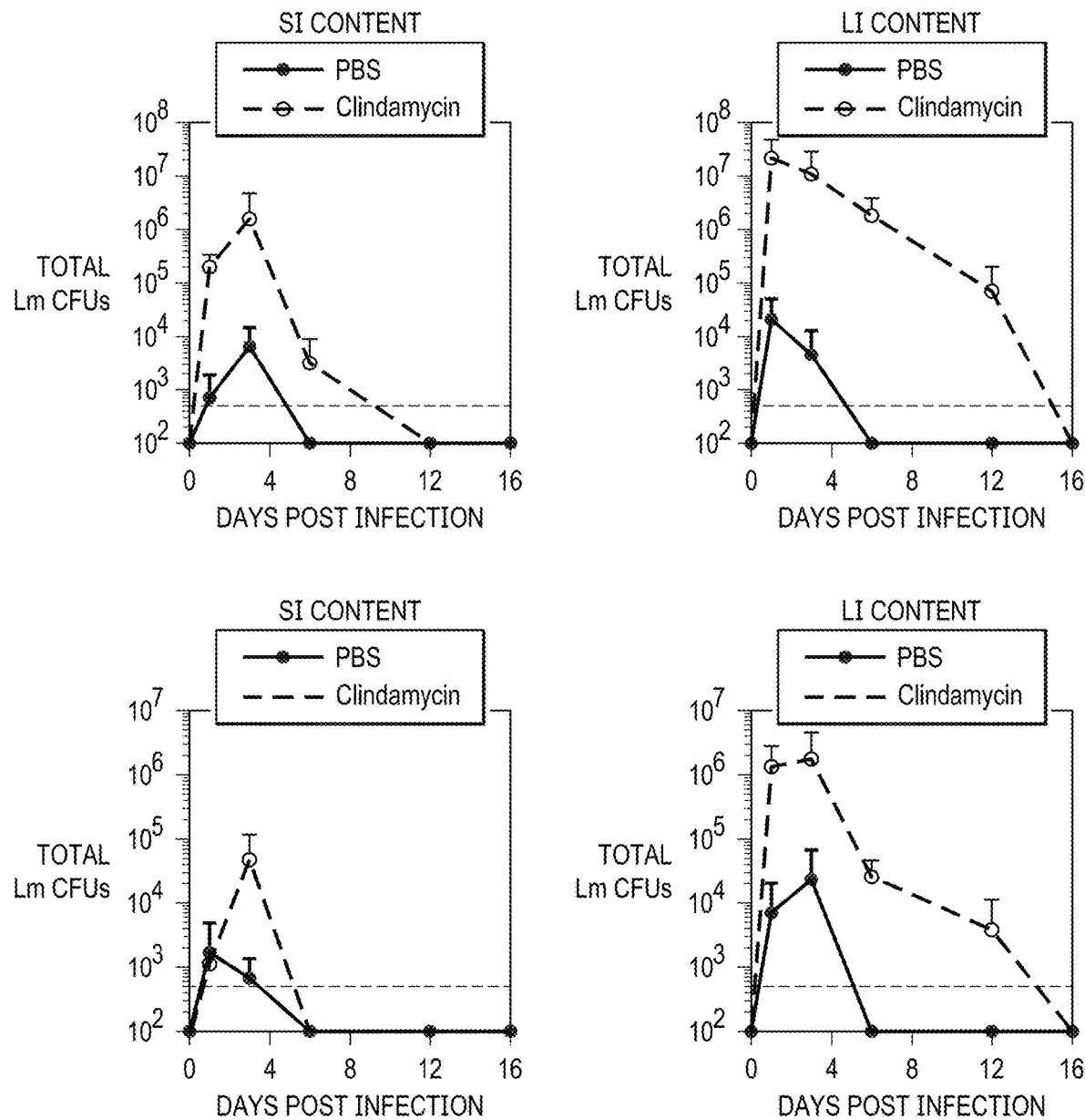
FIG. 1A is a set of graphs showing results for *L. monocytogenes* (Lm) burden in antibiotic-treated mice.

The present invention relates to bacterial compositions that are capable of decreasing the risk of *L. monocytogenes* infection or colonization and for treating *L. monocytogenes* infection or colonization. These bacterial compositions can act in the large intestine of a patient, particularly a human patient. The bacterial compositions, by providing only therapeutic bacteria and other selected agents, may provide improved results as compared to less precise compositions and methods, such as fecal transfer.

For clarity of description, and not by way of limitation, this section is divided into the following subsections:

(i) Therapeutic bacteria;
(ii) Pharmaceutical compositions; and
(iii) Methods of treatment and/or uses of compositions.

The following are terms relevant to the present invention:

"*B. producta*" as used herein refers to any bacterium with a 16S subunit gene having a nucleotide sequence at least 97% similar to that described for strain 2396 at Genbank Accession No: NCBI Reference Sequence: NR_036776.1.

"*C. saccharogumia*" as used herein refers to any bacterium with a 16S subunit gene having a nucleotide sequence at least 97% similar to that described for strain SDG-Mt85-3db at Genbank Accession No.: NCBI Reference Sequence: NR_043550.1.

"*C. ramosum*" as used herein refers to any bacterium with a 16S subunit gene having a nucleotide sequence at least 97% similar to that described for strain DSM 1402 at Genbank Accession No: GenBank: X73440.1.

"*C. hathewayi*" as used herein refers to any bacterium with a 16S subunit gene having a nucleotide sequence at least 97% similar to that described for strain 1313 at Genbank Accession No: NCBI Reference Sequence: NR_036928.1.

An "individual," "subject," or "patient" herein is a vertebrate, such as a human or non-human animal, for example, a mammal. Mammals include humans, non-human primates, farm animals, sport animals, rodents and pets. Human patients include pregnant women, children under two weeks old (newborn children), prematurely born children, adults over seventy years old (elderly adults), adults and children who have recently been administered or are currently being administered antibiotics, and immunocompromised adults and children, such as patients receiving an immunosuppressant drug such a chemotherapeutic or a drug to reduce the risk of transplant rejection. Examples of non-human animal subjects include rodents such as mice, rats, hamsters, and guinea pigs; rabbits; dogs; cats; sheep; pigs; goats; cattle; horses; and non-human primates such as apes and monkeys.

"*L. monocytogenes*" as used herein refers to all variants and strains of the species, except in the case of the Examples, in which particular variants or strains were used as indicated. *L. monocytogenes* includes any bacterium with a 16S subunit gene having a nucleotide sequence at least 97% similar to that of 16S subunit gene sequence contained in NCBI Reference Sequence: NC_017544.1, for *L. monocytogenes* strain 10403s, any bacterium with a p60 gene having a nucleotide sequence at least 95% similar to that of the p60 gene sequence contained in NCBI Reference Sequence: NC_017544.1, for *L. monocytogenes* strain 10403s, and any bacterium exhibiting approximately a 1300 base pair DNA molecule after amplification via PCR using primers having SEQ. ID. No: 1 and SEQ. ID. No. 2, as disclosed in the Examples, under conditions as disclosed in the Examples.

"*L. monocytogenes* colonization" or colonization with *L. monocytogenes*" as used herein designate colonization of a site in the gastrointestinal tract, such as the intestine, particularly the large intestine, of a subject with *L. monocytogenes* without a *L. monocytogenes* infection symptom or without a *L. monocytogenes* infection symptom attributable to *L. monocytogenes* colonization. *L. monocytogenes* can be detectable by the culture of *L. monocytogenes* from or detection of *L. monocytogenes* biomarkers in the feces, intestinal contents, sputum, or blood, cerebrospinal fluid, placental tissue, or organ biopsy of the subject. *L. monocytogenes* biomarkers include *L. monocytogenes*-specific nucleic acids or proteins, including protein fragments, and/or nucleic acid or protein profiles, such as *L. monocytogenes*-specific 16S rRNA or *L. monocytogenes*-specific p60 gene. *L. monocytogenes* biomarkers are detectable at least by sequencing, PCR-based tests, and protein assays, and nucleic and/or protein arrays, as applicable for the particular *L. monocytogenes* biomarker(s).

"*L. monocytogenes* infection" and "infection with *L. monocytogenes*" as used herein designate *L. monocytogenes* colonization and the presence of one or more *L. monocytogenes* infection symptoms. A "*L. monocytogenes* infection symptom" includes include one or more symptoms of listeriosis and/or invasive listeriosis, including abdominal tenderness, abdominal pain, abdominal cramping, diarrhea, nausea, vomiting, fever, chills, fatigue, muscle aches, headache, stiff neck, back ache, confusion, loss of balance, convulsions, sepsis, meningitis, chorioamnionitis, meningoencephalitis, and/or death, and, in pregnant women, placental infection, miscarriage, stillbirth, and/or premature labor.

A "therapeutically effective amount" of a substance as used herein is that amount sufficient to effect beneficial or desired results, including clinical results, and, as such, an "effective amount" depends upon the context in which it is being applied.

In the context of administering a composition to reduce the risk of *L. monocytogenes* infection or colonization and/or increase resistance to *L. monocytogenes* infection or colonization in a subject, including reducing such risk of and/or increasing such resistance to infection in a patient colonized with *L. monocytogenes*, administering a composition to reduce the severity of *L. monocytogenes* infection in a subject, and/or administering a composition to reduce a *L. monocytogenes* infection symptom in a subject, an effective amount of a composition described herein is an amount sufficient to treat a *L. monocytogenes* infection. In some embodiments, an effective amount can decrease the severity of and/or reduce the likelihood of a *L. monocytogenes* infection and/or decrease the likelihood of colonization.

The decrease can be a 10%, 20%, 30%, 40%, 50%, 60%, 70%, 80%, 90%, 95%, 98% or 99% decrease and up to a 100% decreases in colony forming units (CFU) of *L. monocytogenes* in a sample from the subject, such as a gastrointestinal sample, blood, a placenta, particularly a delivered placenta, or an organ biopsy, as compared to an untreated subject with *L. monocytogenes* infection or colonization. The decrease can be a 10%, 20%, 30%, 40%, 50%, 60%, 70%, 80%, 90%, 95%, 98% or 99% decrease and up to a 100% decrease in CFU of *L. monocytogenes* in a sample from the subject, such as a gastrointestinal sample, blood, a placenta, particularly a delivered placenta, an organ biopsy, or cerebrospinal fluid, as compared to the number of CFUs in the subject prior to treatment of the subject.

The decrease can be a 10%, 20%, 30%, 40%, 50%, 60%, 70%, 80%, 90%, 95%, 98% or 99% decrease and up to a 100% decrease in severity of *L. monocytogenes* infection, as demonstrated by amount of a VRE biomarker in a sample from the subject, such as a gastrointestinal sample, blood, a placenta, particularly a delivered placenta, or an organ biopsy, as compared to an untreated subject with *L. monocytogenes* infection or colonization. The decrease can be a 10%, 20%, 30%, 40%, 50%, 60%, 70%, 80%, 90%, 95%, 98% or 99% decrease and up to a 100% decrease in severity of *L. monocytogenes* infection, as demonstrated by amount of a *L. monocytogenes* biomarker in a sample from the subject, such as a gastrointestinal sample, blood, a placenta, particularly a delivered placenta, an organ biopsy, or cerebrospinal fluid as compared to the severity of infection in the subject prior to treatment.

In some embodiments, the decrease is assayed using a blood biomarker. Such biomarkers can be particularly clinically relevant, as they can strongly correlate with absence or treatment of sepsis resulting from *L. monocytogenes* infection and/or invasive listeriosis.

The decrease can be a 10%, 20%, 30%, 40%, 50%, 60%, 70%, 80%, 90%, 95%, 98% or 99% decrease and up to a 100% decrease in progression to *L. monocytogenes* infection based on the development of a *L. monocytogenes* infection symptom, as compared to an untreated subject with *L. monocytogenes* colonization.

An effective amount with respect to *L. monocytogenes* infection can be administered in one or more administrations.

An effective amount of therapeutic bacteria can be, for each of the four therapeutic bacteria individually, at least $10^5$ bacteria, or at least $10^6$ bacteria, or at least $10^7$ bacteria, or at least $10^8$ bacteria, or at least $10^9$ bacteria and up to $10^{10}$ bacteria, or $10^{11}$ bacteria, or $10^{12}$ bacteria, or $10^{15}$ bacteria.

As used herein, and as understood in the art, "treatment" or "treating" is an approach for obtaining beneficial or desired results, including clinical results. For purposes of this subject matter, beneficial or desired clinical results include, but are not limited to, prevention, alleviation or amelioration of one or more symptoms, diminishment of extent of disease, stabilized (i.e., not worsening) state of disease, prevention of disease, delay or slowing of disease progression, reduced risk of recurrence of disease, and/or amelioration or palliation of the disease state.

The disease state herein can include *L. monocytogenes* infection or colonization, and/or one or more *L. monocytogenes* infection symptoms. The decrease can be a 10%, 20%, 30%, 40%, 50%, 60%, 70%, 80%, 90%, 95%, 98% or 99% decrease and up to a 100% decrease in severity of *L. monocytogenes* infection or colonization or *L. monocyto-*

*genes* infection symptoms, such as a decrease in fecal CFU of *L. monocytogenes*, a decrease in fecal *L. monocytogenes* biomarker, and/or a decrease in blood *L. monocytogenes* biomarker as compared to an untreated subject with *L. monocytogenes* infection or colonization or the same patient prior to treatment. "Treatment" can mean reducing the risk of *L. monocytogenes* infection or colonization, and/or increasing resistance to *L. monocytogenes* infection in a patient colonized with *L. monocytogenes*, and/or reducing the severity of *L. monocytogenes* infection or a symptom thereof in a subject or population.

"Treatment" can also mean a decrease in progression from colonization to infection in a patient as compared to a similar patient without treatment or a similar patient population with *L. monocytogenes* colonization and without treatment.

"Treatment" can also mean a decrease in progression from colonization or a non-invasive infection to invasive listeriosis as compared to a to a similar patient without treatment or a similar patient population with *L. monocytogenes* infection or colonization and without treatment.

"Treatment" can also mean a decrease in a specific, and, in some embodiments, readily detectable clinical outcome as compared to a to a similar patient without treatment or a similar patient population with *L. monocytogenes* infection or colonization and without treatment. For example, "treatment" can mean a decrease in miscarriage, stillbirth, or premature labor in pregnant women as compared to a to a similar patient without treatment or a similar patient population with *L. monocytogenes* infection or colonization and without treatment. Similarly, "treatment" can mean a decrease in likelihood of infection of a newborn child of a pregnant woman as compared to a to a similar patient without treatment or a similar patient population with *L. monocytogenes* infection or colonization and without treatment.

"Treatment" can also mean a decrease in death, particularly in adults over newborn children or elderly adults, as compared to a to a similar patient without treatment or a similar patient population with *L. monocytogenes* infection or colonization and without treatment. "Treatment" can also mean a decrease in the quantity of *L. monocytogenes* detectable in a patient or population of patients after treatment as compared to a similar sample from the patient or population of patients prior to treatment, for example a quantitative decrease in the titer of *L. monocytogenes* detected in a fecal sample.

Therapeutic Bacteria

Therapeutic bacteria as described herein include at least one of, at least two of, at least three of, or all at least four of isolated or purified *C. saccharogumia, C. ramosum, C. hathewayi*, and *B. producta*, in any combinations. More particularly, the therapeutic bacteria as described herein may include at least one of, at least two of, or all three of isolated or purified *C. ramosum, C. hathewayi*, and *B. producta*.

In certain embodiments, therapeutic bacteria treat *L. monocytogenes* infection or *L. monocytogenes* colonization in a subject, and/or reduce the risk of *L. monocytogenes* infection or *L. monocytogenes* colonization in a subject, and/or increase resistance to *L. monocytogenes* infection or *L. monocytogenes* colonization in a subject, and/or decrease the severity of *L. monocytogenes* infection in a subject, and/or decrease the amount of *L. monocytogenes* colonizing a subject.

In certain embodiments, the compositions described herein comprise, consist essentially of, or consist of at least one, or at least two therapeutic bacteria, or spores thereof, including recombinant therapeutic bacteria, non-recombinant bacteria and bacterial clusters containing therapeutic bacteria.

In certain embodiments, the compositions described herein comprise, consist essentially of, or consist of at least one or at least two therapeutic bacteria, or spores thereof, including recombinant therapeutic bacteria, non-recombinant bacteria and bacterial clusters containing therapeutic bacteria in a formulation for administration to a subject.

In certain embodiments, the compositions described herein comprise, consist essentially of, or consist of a mixture of at least two therapeutic bacteria, or spores thereof, including recombinant therapeutic bacteria, non-recombinant bacteria and bacterial clusters containing therapeutic bacteria.

In certain embodiments, the compositions described herein comprise, consist essentially of, or consist of a mixture of at least two therapeutic bacteria, or spores thereof, including recombinant therapeutic bacteria, non-recombinant bacteria and bacterial clusters containing therapeutic bacteria in a formulation for administration to a subject.

In embodiments that comprise, consist essentially of, or consist of at least two isolated therapeutic bacteria, or methods using such a composition a synergistic effect may be observed.

In some embodiments, all bacteria in the composition are recombinant. In other embodiments, all bacteria in the composition are non-recombinant. Other compositions include both recombinant and non-recombinant bacteria.

Applicants have discovered that the risk and/or severity of *L. monocytogenes* infection or colonization, or progression to invasive listeriosis can be reduced by the presence of therapeutic bacteria in the intestines of a patient, particularly in the large intestine of a patient, particularly a human patient. Without limiting the invention to a specific mode of action, these therapeutic bacteria can have an anti-*L. monocytogenes* activity in the large intestine of the patient that is independent of any anti-*L. monocytogenes* activity mediated by the patient's immune system.

The therapeutic bacteria can be in a formulation suitable for administration to a subject. These forms include a desiccated form and/or as part of a solid pharmaceutical dosage form, such as a capsule or tablet.

The therapeutic bacteria in the composition can be in the vegetative state or spores, or a mixture thereof.

The therapeutic bacteria described herein can be modified, for example, by introducing one or more nucleic acids into the bacteria, thereby producing recombinant bacteria. Such nucleic acids can include, for example, an antibiotic resistance gene, an antibiotic susceptibility gene, a protease gene, a glycosidase, and/or a bile salt hydrolase gene, as described herein.

In certain embodiments, the composition comprises, consists essentially of, or consists of therapeutic bacteria as a constituent in a mixture of types of bacteria, optionally including one or more probiotic bacteria or probiotic yeast, optionally in a formulation for administration to a subject.

"Probiotic bacteria" as used herein include any bacteria that have a beneficial effect to a subject when located in the subject's gastrointestinal system, such as a *Lactobacillus* or a *Bifidobacterium*.

"Probiotic yeast" as used herein include any yeast that can have a beneficial effect to a subject when located in the subject's gastrointestinal system, such as a *Saccharomyces*.

All therapeutic bacteria described herein, whether recombinant or non-recombinant, isolated or in a mixture, can be cultured using techniques known in the art, including techniques to produce bacteria or spores thereof or bacterial clusters suitable for administration to a subject.

Pharmaceutical Compositions

Therapeutic bacteria compositions described herein can be present in pharmaceutical compositions. The pharmaceutical compositions can be in the form of a liquid, a suspension, a dried (e.g., lyophilized) powder, a tablet, a capsule, a suppository, or an enema fluid, and can be administered orally, nasogastrically, or rectally.

Such pharmaceutical compositions can further include at least one other agent, such as a stabilizing compound or additional therapeutic agent, and can be administered in any sterile, biocompatible pharmaceutical carrier, including, but not limited to, saline, buffered saline, dextrose, and water. The pharmaceutical compositions can also further include an excipient. The composition can be in a liquid or lyophilized form and includes a diluent (Tris, citrate, acetate or phosphate buffers) having various pH values and ionic strengths, solubilizer such as Tween® or polysorbate, carriers such as human serum albumin or gelatin, preservatives such as thimerosal, parabens, benzylalconium chloride or benzyl alcohol, antioxidants such as ascorbic acid or sodium metabisulfite, and other components such as lysine, glycine, polyethylene glycol, cocoa butter, glycerol. Selection of a particular composition will depend upon a number of factors, including the condition being treated, the route of administration and the pharmacokinetic parameters desired. A more extensive survey of components suitable for pharmaceutical compositions is found in *Remington's Pharmaceutical Sciences,* 18th ed. A. R. Gennaro, ed. Mack, Easton, Pa. (1980).

In certain embodiments, the methods and compositions of the present invention find use in treating *L. monocytogenes* infection or colonization. At least one or at least two therapeutic bacteria can be administered to the patient in a pharmaceutically acceptable carrier. The route of administration eventually chosen will depend upon a number of factors and can be ascertained by one skilled in the art.

Pharmaceutical compositions suitable for use in the present invention include compositions where the therapeutic bacteria and other active ingredients are contained in an effective amount to achieve the intended purpose. The amount can vary from one individual to another and will depend upon a number of factors, including the overall physical condition of the patient, e.g., severity of the *L. monocytogenes* infection, stage of the disease or condition, the severity of the disease or condition, the patient's size, body surface area, age, the particular compound to be administered, sex, time and route of administration, general health, and interaction with other drugs being concurrently administered, whether *L. monocytogenes* infection or *L. monocytogenes* colonization has occurred, and/or whether the composition is being administered prophylactically.

Therapeutic bacteria compositions described herein can be provided in a food product, for example, a yogurt food product. In certain embodiments, a "food product" means a product or composition that is intended for consumption by a human or a non-human animal. Such food products include any food, feed, snack, food supplement, liquid, beverage, treat, toy (chewable and/or consumable toys), meal substitute or meal replacement.

Methods of Treatment and Use of Therapeutic Bacteria

The present disclosure also provides for a method of treating *L. monocytogenes* infection or colonization by administering, to a subject in need of such treatment, an effective amount of a composition described herein. The composition can comprise, consist essentially of, or consist of at least one or at least two therapeutic bacteria as described herein, optionally in a formulation suitable for administration to a subject.

The present disclosure also provides for the use of a composition that comprises, consists essentially of, or consists of at least one or at least two therapeutic bacteria as described herein, optionally in a formulation suitable for administration to a subject, in treating *L. monocytogenes* infection or colonization. The use can be further characterized by aspects of the methods described above and elsewhere herein.

A subject treated with therapeutic bacteria as described herein can be concurrently or sequentially treated with at one or more agents that reduce the risk of and/or ameliorates *L. monocytogenes* infection colonization, for example, but not limited to, one or more antibiotic for example, but not limited to, ampicillin, gentamicin, and/or trimethoprim-sulfamethoxazole and/or a probiotic bacteria or probiotic yeast including for example, but not limited to, *Lactobacillus acidophilus, Lactobacillus casei, Bifidobacterium, Streptococcus thermophilus,* and/or *Saccharomyces boulardii.*

Single or multiple administrations of formulations can be given depending on the dosage and frequency as required and tolerated by the patient. In certain embodiments, the formulations should provide a sufficient quantity of active agent to effectively treat the *L. monocytogenes* infection or colonization.

Methods of the present disclosure include treating *L. monocytogenes* infection or colonization early after exposure of the patient to *L. monocytogenes*, or early after its introduction into the patient. For example, if a contaminated food source is identified, patients who may have consumed it may be treated, particularly within one day, two days, five days, one week, or two weeks of exposure. Similar time frames may constitute early treatment with respect to other known exposures or introductions.

During the early phases of intestinal infection, such as when the intestines are merely colonized with *L. monocytogenes,* bacteria may be shed from the tips of infected villi into the lumen and then penetrate the epithelium at different locations, thus extending tissue invasion and resulting in invasive listeriosis. The loss of microbiota-mediated colonization resistance in immunocompromised patients may further amplify this *L. monocytogenes* expansion. Accordingly, treatment of immunocompromised patients according to the present disclosure may limit or avoid this expansion and thereby limit or avoid the development of infection or invasive listeriosis.

Although the more established view holds that *L. monocytogenes* infection or colonization primarily occurs in the small intestine, the present disclosure suggests that the large intestine may be the more clinically relevant organ for infection or colonization. Accordingly, methods of the present disclosure, particularly include treating *L. monocytogenes* infection or colonization in the large intestine, including a reduction of *L. monocytogenes* in the lumen of the large intestine.

Residual amounts of *L. monocytogenes* in the intestinal lumen may persist up to three weeks or longer even in subjects in which therapeutic bacteria are present. This colonization can allow *L. monocytogenes* to expand, particularly if the subject becomes immunocompromised. Accordingly, methods of the present disclosure include treating patients after administration of an immunocompromising agent, such as an antibiotic, a chemotherapeutic, or an immune suppressant, such as an anti-transplant rejection drug. Treatment may be concurrent with, one day after, two days after, one week after, or two weeks after administration of the immunocompromising agent.

Without limiting the invention to any particular mechanism or set of mechanisms, multiple mechanisms may account for such inhibition of *L. monocytogenes* by the therapeutic bacteria, possibly reflecting the different commensal communities represented along the GI tract. Competition for nutrients may be a crucial factor promoting growth restriction of *L. monocytogenes* in the small intestine. Toxin secretion may also play a role. Anaerobes from the large intestine have not been previously associated with protection from *L. monocytogenes*. These commensals may operate through mechanisms that do not involve secretion of toxins or competition for nutrients. Such alternative mechanisms of inhibition may include contact-dependent inhibition.

The present disclosure also provides methods of diagnosing or identifying a subject at risk for *L. monocytogenes* infection or colonization. Such methods include detecting the presence of or concentration of one or more of the therapeutic bacteria in a gastrointestinal sample, such as a fecal sample, from the subject. The absence of one or more of the therapeutic bacteria, or presence only at a low concentration, may indicate that a subject is at risk for *L. monocytogenes* infection or colonization. The concentration may be further indicative, with lower concentrations correlating with increased risk. Similarly, the number of therapeutic bacteria absent or at low concentration may correlate with increased risk, with more therapeutic bacteria being absent correlating with greater risk.

The present disclosure also provides methods of determining appropriate therapeutic bacteria for treatments as described herein. Such methods include detecting the presence of or concentration of one or more of the therapeutic bacteria in a gastrointestinal sample, such as a fecal sample, from the subject before treatment. Therapeutic bacteria already present in the subject, or present at or above a threshold concentration level, may be omitted from the therapeutic bacteria compositions administered to the subject.

The present disclosure further provides methods of monitoring treatment with therapeutic bacteria as described herein. Such methods include detecting the presence of or concentration of one or more of the therapeutic bacteria in a gastrointestinal sample, such as a fecal sample, from the subject during or after treatment. Treatment may be continued, at least with the absent or low-concentration bacteria, if some therapeutic bacteria are still absent from the subject or present only at low concentrations after an earlier treatment. Treatment may be ceased, at least with respect to present or threshold-concentration-level bacteria if some therapeutic bacteria are present in the subject or present at or above a threshold concentration level after an earlier treatment.

In the various methods described above, a low-concentration is one below a threshold-concentration level, which may be defined as a level that is therapeutically effective when the relevant bacteria is present with the other therapeutic bacteria.

In the various methods described above, absence or low concentration of *C. saccharogumia* may not be indicative of a need to administer any treatments or additional treatments, as, although *C. saccharogumia* may play a role in *L. monocytogenes* therapy, it may be lost after time without negative effect.

EXAMPLES

The presently disclosed subject matter will be better understood by reference to the following Examples, which are provided as exemplary of the invention, and not by way of limitation.

Mice: Throughout these Examples, mice are used as experimental models for *L. monocytogenes* infection or colonization. Mice are considered relatively resistant to oral infection with *L. monocytogenes* but can develop disseminated infection upon oral inoculation with very high doses of *L. monocytogenes*. Dissemination from the intestine in invasive listeriosis requires *L. monocytogenes* to traverse the intestinal epithelium, either by transcytosis of M cells into Peyer's patches, or by binding of the bacterial invasion protein internalin A (InlA) with its ligand, E-cadherin (E-cad). The relative resistance of mice, compared to humans, to oral infection with *L. monocytogenes* results, in part, from reduced affinity of InlA for murine, as opposed to human E-cad. However, even wild type (WT) mice are sufficiently susceptible to *L. monocytogenes* infection or colonization to service a models for humans and other mammals.

In addition, mice with various immune system impairments, making them more susceptible to *L. monocytogenes* infection or colonization or otherwise useful in studying non-immune-mediated resistance to *L. monocytogenes* were used in some examples. Rag1−/− Ifng−/− mice lack mature T cells and B cells and do not produce Interferon γ, resulting in lower MHCII and NK cell levels, among other immune system impairments. Rag−/−IL17−/− mice lack mature T and B cells and do not produce Interleukin 17, resulting in other immune system impairments. Rag2−/−IL2rg−/− (Raggc) mice exhibit T cell, B cell and NK cell immunodeficiencies.

Antibiotic Treatments: Three different antibiotic treatments were used in these Examples: 1) a single intraperitoneal (i.p.) injection of clindamycin (200 μg/mouse in phosphate buffered saline (PBS)); 2) a single dose of streptomycin (ThermoFisher) (20 mg/mouse in PBS, except in Example 6) administered by oral gavage; and 3) a single dose of metronidazole (SIGMA), neomycin (SIGMA) and vancomycin (NOVAPLUS) (3.5 mg each/mouse in PBS) administered by oral gavage, followed by a single injection of clindamycin 3 days later (MNVC treatment).

Chemotherapy: Chemotherapy used in these Examples was composed of cyclophosphamide (SIGMA-ALDRICH C0768) (1.8 mg/mouse, approximately 100 mg/kg) and doxorubicin (Pfizer 0069-3030-20) (0.27 mg/mouse, approximately 15 mg/kg) and administered together via i.p injection in 200 μl total volume. Chemotherapy was administered twice one week apart; bleeding or infections were performed one day following the second administration (except in Example 4, FIG. 8F). *L. monocytogenes* colonies were identified by their characteristic morphology and occasionally confirmed by Gram staining and PCR for the p60 gene.

*L. monocytogenes* Infection, CFU enumeration and PCR confirmation: *L. monocytogenes* strain 10403s was used throughout these Examples. This does not imply that only that strain is "*L. monocytogenes*" as discussed elsewhere in this specification and claims.

Frozen aliquots of bacteria were freshly inoculated into Brain Heart Infusion (BHI) broth and grown to optical density (OD) 0.1-0.4 (OD=0.1 corresponds to $2*10^8$ CFUs/ml), washed once in PBS and resuspended in PBS for inoculation. Doses varied depending on the experiment. *L. monocytogenes* was administered by oral gavage in all in vivo experiments.

To enumerate *L. monocytogenes* growth in mouse tissue, collected organs were resuspended in PBS Triton X-100 (Fisher) 0.05%, homogenized for 30 seconds to 1 minute with a Power Gen 125 homogenizer (Fisher Scientific) (power level: 5). Metal probes were washed in between samples through 2 immersions in ethanol and one in PBS for 10-15 seconds each. Serial dilutions of the homogenates were prepared in PBS Triton and plated on BHI agar plates supplemented with streptomycin (100 µg/ml) and nalidixic acid (50 µg/ml). Colonies were enumerated after 24 h of incubation at 37° C.

For CFU enumeration in the intestinal wall, after excision, small and large intestine were separated, cleared of content by squeezing with forceps, cut longitudinally and washed vigorously 4-6 times (10s vortex or manual shaking) in ice-cold PBS. The washed tissues were then processed as described above.

For CFU enumeration in intestinal content and fecal pellets, starting material was weighted (unless total CFU amount was calculated) and resuspended in PBS to a concentration of 100 mg/ml. Serial dilutions of the original suspension were plated. Roughly 10% of plates from small and large intestine content and tissue displayed a second type of bacterial colony, clearly distinguishable from *L. monocytogenes* colonies based on size and color. In particular, contaminating colonies were much smaller than *L. monocytogenes* colonies and of a brighter white color. To confirm the identity of *L. monocytogenes* colonies, several colonies of each type from every contaminated plate were picked and subjected to PCR for the *L. monocytogenes* p60 gene. A clear band of approximately 1300 bp was always detected in PCRs of *L. monocytogenes* colonies, but not in contaminating colonies (FIG. 2B), thus confirming *L. monocytogenes* identity as determined by colony color and morphology. Contaminant colonies were not included into CFU counts.

*L. monocytogenes* was also confirmed, in some examples, via PCR of the p60 gene. The Sequence of the p60 PCR primers was: 5'START: GCG GTA ACA GCA TTT GCT GCT CCA ACA ATC (SEQ. ID. No. 1) and 3' END: GC CAT TGT CTT GCG CGT TAA TCA TTT GAC (SEQ. ID. No. 2). Amplification conditions were 30 cycles (95° C.×1'; 50° C.×1'; 65° C.×2.5'), 72° C.×5', hold 4° C.

Pathology score: Pathology scores used in these examples were calculated using methods previously published (Abt M C, Lewis B B, Caballero S, Xiong H, Carter R A, Susac B, Ling L, Leiner I, and Pamer E G. Innate Immune Defenses Mediated by Two ILC Subsets Are Critical for Protection against Acute *Clostridium difficile* Infection. Cell host & microbe. 2015; 18(1):27-37). After infection, mice were monitored and scored for disease severity by four parameters: weight loss (>95% of initial weight=0, 95%-90% initial weight=1, 90%-80% initial weight=2, <80%=3), surface body temperature (>32° C.=0, 32° C.-30° C.=1, 30° C.-28° C.=2, <28° C.=3), diarrhea severity (formed pellets=0, loose pellets=0, liquidly discharge=2, no pellets/caked to fur=3), morbidity (score of 1 for each symptoms with max score of 3; ruffled fur, hunched back, lethargy, ocular discharge).

Blood Cell Collection and Flow Cytometry

Blood used in these Examples was obtained by tail bleeding. Red blood cell lysis was performed by 3 consecutive incubations in RBC lysis buffer (0.15 M NH4Cl=1 mM $NaHCO_3$ in dH2O) for 5'. Lymphocytes were counted and subjected to viability staining (Fixable Aqua Dead Cell staining, Life Technologies, #L34957) and subsequently to receptor Fc blockade (BD #553142). Staining was performed using the following antibodies: CD45 (clone 30-F11 eBioscience), CD8b (clone YTS156.7.7, BioLegend), CD11b (clone RM2817, Thermo Fisher), Ly6c (clone AL-21, BD), CD3ε (clone 145-2C11, BD), CD19 (clone 1D3, BD), CD90.2 (53-2.1, BD), CD127 (clone A7R34, BD). For flow cytometry analysis in these Examples, samples were fixed (IC Fixation Buffer, eBioscience), washed, resuspended in FACS buffer and acquired with an LSRII flow cytometer (BD) either immediately or on the following day.

DNA Extraction and 16s Sequencing

DNA extraction from fecal pellets and intestinal content were performed in these Examples as previously described (Ubeda C, Lipuma L, Gobourne A, Viale A, Leiner I, Equinda M, Khanin R, and Pamer E G. Familial transmission rather than defective innate immunity shapes the distinct intestinal microbiota of TLR-deficient mice. The Journal of experimental medicine. 2012; 209(8):1445-56). Briefly, a frozen aliquot (~100 mg) of each sample was suspended, while frozen, in a solution containing 500 µl of extraction buffer (200 mM Tris, pH 8.0/200 mM NaCl/20 mM EDTA), 200 µl of 20% SDS, 500 µl of phenol:chloroform:isoamyl alcohol (24:24:1), and 500 µl of 0.1-mm diameter zirconia/silica beads (BioSpec Products).

Microbial cells were lysed by mechanical disruption with a bead beater (BioSpec Products) for 2 min, after which two rounds of phenol:chloroform:isoamyl alcohol extraction were performed. DNA was precipitated with ethanol and re-suspended in 50 µl of TE buffer with 100 µg/ml RNase. The isolated DNA was subjected to additional purification with QIAamp Mini Spin Columns (Qiagen). For each sample, duplicate 50 µl PCR reactions were performed, each containing 50 ng of purified DNA, 0.2 mM dNTPs, 1.5 mM MgCl2, 2.5 U Platinum Taq DNA polymerase, 2.5 µl of 10×PCR buffer, and 0.5 µM of each primer designed to amplify the V4-V5: 563F (AYTGGGYDTAAAGNG) (SEQ. ID. No.: 3) and 926R (CCGTCAATTYHTTTRAGT) (SEQ. ID. No.: 4). A unique 12-base Golay barcode preceded the primers for sample identification (Caporaso J G, Lauber C L, Walters W A, Berg-Lyons D, Huntley J, Fierer N, Owens S M, Betley J, Fraser L, Bauer M, et al. Ultra-high-throughput microbial community analysis on the Illumina HiSeq and MiSeq platforms. The ISME journal. 2012; 6(8):1621-4), and 1-8 additional nucleotides were placed in front of the barcode to offset the sequencing of the primers. Cycling conditions were 94° C. for 3 minutes, followed by 27 cycles of 94° C. for 50 seconds, 51° C. for 30 seconds, and 72° C. for 1 minute. 72° C. for 5 min was used for the final elongation step.

Replicate PCRs were pooled, and amplicons were purified using the Qiaquick PCR Purification Kit (Qiagen). PCR products were quantified and pooled at equimolar amounts before Illumina barcodes and adaptors were ligated on using the Illumina TruSeq Sample Preparation protocol. The completed library was sequenced on an Illumina Miseq platform following the Illumina recommended procedures with a paired end 250×250 bp kit. The 16S (V4-V5) paired-end reads were merged and demultiplexed. The UPARSE pipeline (80. Edgar R C. UPARSE: highly accurate OTU sequences from microbial amplicon reads. Nature methods. 2013; 10(10):996-8) was used to: (1) perform error filtering, using maximum expected error (Emax=1)(Edgar R C, and Flyvbjerg H. Error filtering, pair assembly and error correction for next-generation sequencing reads. Bioinformatics. 2015; 31(21):3476-82)), (2) group sequences into operational taxonomic units (OTUs) of 97% distance-based similarity, (3) identify and remove potential chimeric sequences, using both de novo and reference-based methods. Sequencing data was analyzed and processed using the MOTHUR pipeline (Schloss P D, Westcott S L, Ryabin T, Hall J R, Hartmann M, Hollister E B, Lesniewski R A, Oakley B B, Parks D H, Robinson C J, et al. Introducing mothur: open-source, platform-independent, community-supported software for describing and comparing microbial communities. Appl Environ Microbiol. 2009; 75(23):7537-41), and operational taxonomical units (OTU) were classified using a modified version of the Greengenes database (DeSantis T Z, Hugenholtz P, Larsen N, Rojas M, Brodie E L, Keller K, Huber T, Dalevi D, Hu P, and Andersen G L. Greengenes, a chimera-checked 16S rRNA gene database and workbench compatible with ARB. Appl Environ Microbiol. 2006; 72(7):5069-72).

Anaerobic Culturing and Ex Vivo Competition Experiments

In these Examples, commensal anaerobes and intestinal content (unless otherwise stated in the specific Example or experiment) were cultured using in an anaerobic incubator (Coylabs) at 37° C., using reagents that had been reduced for at least 12 h. For assessment of *L. monocytogenes* survival in vitro, intestinal content or fecal pellets were resuspended at 100 mg/ml in reduced PBS, and inoculated with *L. monocytogenes* (inoculum size indicated in Figure legends) in 100 ul total using 96 well plates with U bottom. *Listeria* survival was assessed after 24, 48 or 72 h. In some experiments, the intestinal suspension was sterile filtered (0.22 um) either directly or following a 24 h culture at 37° C.

Bacterial isolates assessed for anti-*L. monocytogenes* activity included: L. gasseri JV-V03, *C. aldenense* WAL-1872 and *R. gnavus* CC55_001C (BEI resources); *C. innocuum* and *B. producta* (I) isolated in house from mouse intestinal content; *C. ramosum*, *C. saccharogumia*, Clostridiales 1_7_47FAA, *C. hathewayi*, *C. bolteae*, *C. aldenense*, *C. asparagiforme*, Ruminococcus sp. ID8, *R. gnavus*, *C. scindens*, Lachnospiraceae 3_1_57FAA_CT1, Lachnospiraceae 7_1_58 FAA, *C. indolis*, Clostridium sp. 7_3_54FAA, *E. contortum*, *B. producta* (II) isolated by Honda and colleagues from human stool (Atarashi K, Tanoue T, Oshima K, Suda W, Nagano Y, Nishikawa H, Fukuda S, Saito T, Narushima S, Hase K, et al. Treg induction by a rationally selected mixture of Clostridia strains from the human microbiota. Nature. 2013; 500 (7461):232-6).

All bacteria were grown overnight in BHI supplemented with yeast extract 5 g/l and L-cysteine 1 g/l (BD), with the exception of L. gasseri which was grown in MRS broth (Difco). Bacterial species present in the original panel of Honda and colleagues that were not included in the analysis grew poorly in modified BHI.

To assess anti-listerial activity, commensals of choice were inoculated at 013=0.1 into either medium or autoclaved cecal content together with 1000 *L. monocytogenes* CFUs, and residual *Listeria* CFUs were enumerated 24 h later.

Reconstitution of GF Mice

In some Examples GF mice were reconstituted. The GF mice maintained in isolators until the day of reconstitution. Upon transfer to a specific pathogen free (SPF) facility, mice were reconstituted via oral gavage with comparable amounts of Clostridiales of interest (*C. ramosum*, *C. saccharogumia*, *C. hathewayi* and *B. producta* (I)) of approximately $1-3*10^6$/bacterium/mouse, resuspended in 200 µl of reduced PBS.

Alternatively, GF mice were reconstituted with a suspension in reduced PBS of a fecal pellet from MNVC-treated mice (pellet collected 1 day after clindamycin treatment, 1 pellet per ml, 200 µl/mouse). Engraftment was confirmed by plating of fecal pellets onto Columbia Agar Plates with 5% Sheep Blood (BD, L007369) in anaerobic chamber, 2 days post reconstitution.

Statistical and Data Analysis

Data are presented in these Examples and the related Figures as mean±SD. Analyses were performed using GraphPad Prism version 7.0a or R-3.3.2.pkg. Statistical tests used included: Mann-Whitney test for two group comparisons, Kruskall-Wallis test with Dunn's multiple comparisons for three or more group comparisons, two-way ANOVA for time courses, and Log-Rank test for survival. Significance values are indicated as follow: *$p<0.05$, $p<0.01$, *$p<0.001$, ****$p<0.0001$. Spearman correlations were calculated using the function 'cor.test' in the R 'stats' package, method="spearman"; significance values were corrected using Benjamini-Hochberg (BH) procedure, FDR<0.05. PCoA was performed using the 'ordinate' function in the R package 'phyloseq', with method="PCoA", distance="JSD".

Example 1: Antibiotic Treatment Results in Increased Susceptibility to *L. monocytogenes* Infection Various antibiotic treatments were administered to mice to determine their effects on resistance to *L. monocytogenes* infection. Results are presented in FIGS. 1-4. To determine the extent to which the intestinal microbiota provides resistance against oral infection with *L. monocytogenes*, C57BL/6 mice from Jackson Laboratories were treated with one dose of clindamycin followed 24 hours later by oral gavage with a sub-lethal dose of *L. monocytogenes*. Clindamycin treatment markedly increased the duration and magnitude of *L. monocytogenes* carriage in the intestinal lumen and tissue (FIG. 1A).

FIG. 1A shows *L. monocytogenes* (Lm) burden in antibiotic-treated mice. Wild-type (WT) mice were treated with a single intraperitoneal (i.p.) injection of clindamycin and infected orally 24 h later with $10^7$ Lm 10403s colony forming units (CFUs). At each time point animals were euthanized and the total number of Lm CFUs was determined by plating homogenized organs or intestinal content. n=4 per time point, from two independent experiments.

Figure 1B:
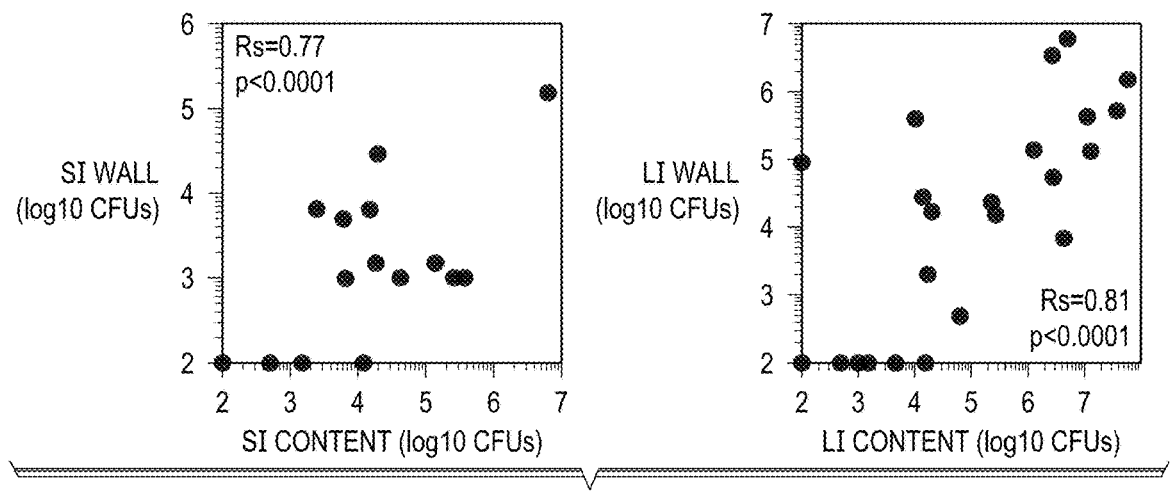
FIG. 1B is a set of graphs showing the Spearman correlation between Lm CFUs recovered from the intestinal content and wall for mice shown in FIG. 1A, for small and large intestine.

The density of *L. monocytogenes* CFUs in the intestinal lumen directly correlated with pathogen burden in the intestinal wall (FIG. 1B).

FIG. 1B shows the Spearman correlation between Lm CFUs recovered from the intestinal content and wall for mice shown in FIG. 1A, for small and large intestine.

Colonies recovered on selective growth plates were further screened by PCR for the *L. monocytogenes* p60 gene (FIG. 2). FIG. 2 provides confirmation of *L. monocytogenes* CFUs identity by selective plating, colony morphology, and PCR.

Figure 2B:
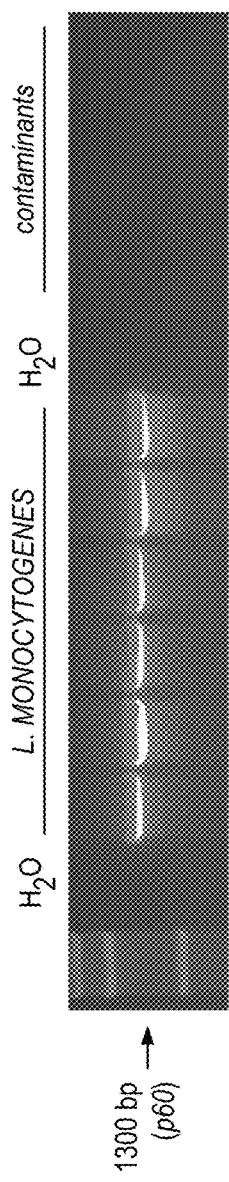
FIG. 2B is an image of representative PCR products obtained for confirmation of colony identity of colonies as shown in FIG. 2A.
Figure 2A:
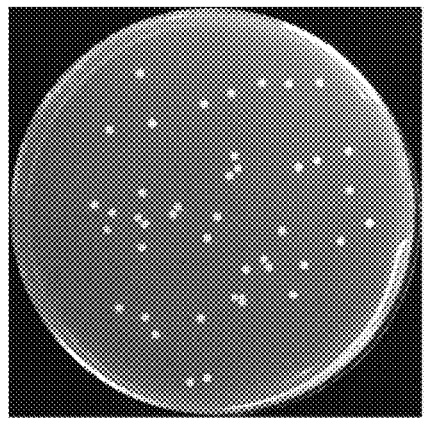
FIG. 2A is photograph of a representative agar culture of diluted large intestinal content from a *L. monocytogenes* infected mouse.

FIG. 2A is a photograph of a representative agar culture of diluted large intestinal content from *L. monocytogenes* 10403s infected mouse on day 1 post infection. Plating was performed on BH1-agar medium supplemented with streptomycin and nalidixic acid. Colonies were analyzed and counted after 24-36 h of incubation, and had a circular morphology, small size and ivory-white color. Colony morphology was similar in plate cultures from different organs.

FIG. 2B shows representative PCR products obtained for confirmation of colony identity, run on 1% agarose gel. Colonies were picked from plates as depicted in (A) and added to PCR mix in tubes. The reaction was designed to amplify a 1300 bp fragment of the *Listeria*-specific gene p60. Occasionally, smaller and brighter white colonies appeared on plates; however such colonies were found to be Gram+ cocci that did not amplify when screened by PCR (here called contaminants). Aberrant colonies were not included in the calculation of the *Listeria* burden.

Figure 3B:
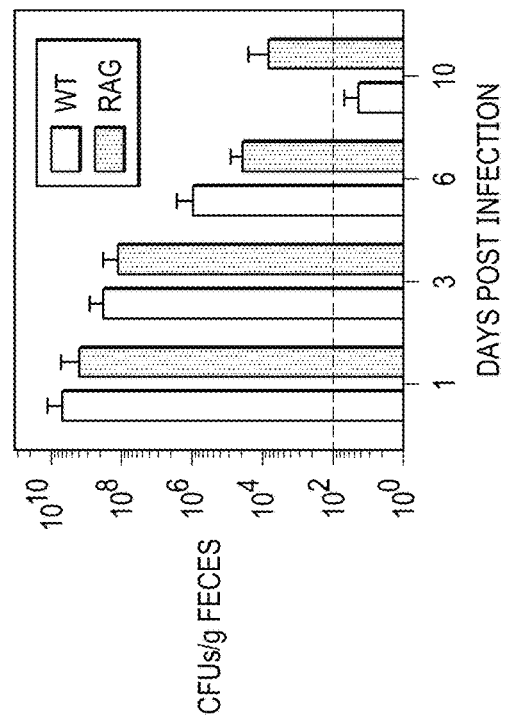
FIG. 3B is a graph of *L. monocytogenes* content in feces of mice of FIG. 3A.
Figure 3A:
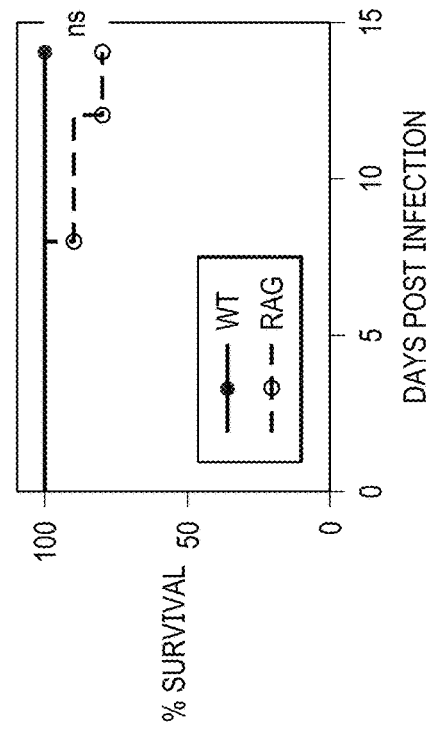
FIG. 3A is a graph of survival of mice administered antibiotics and *L. monocytogenes;*
Figure 4:
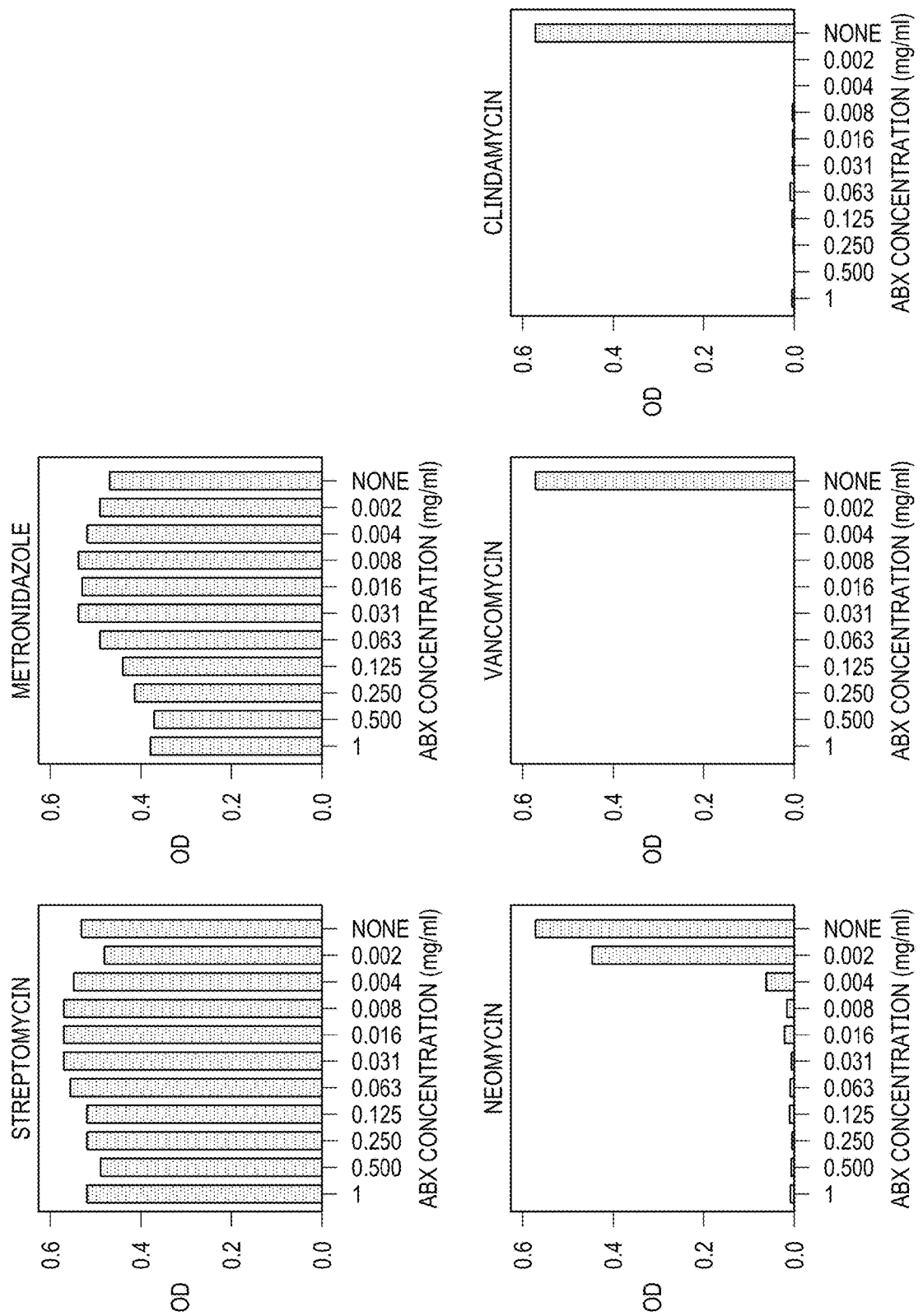
FIG. 4 is set of graphs forming an antibiotic-sensitivity profile of *L. monocytogenes;*

FIG. 3 illustrates that reduction of *L. monocytogenes* burden in the intestinal lumen is independent of adaptive immunity. WT and Rag-/- (Rag) mice were co-housed for three weeks, then injected i.p. with a single dose of clindamycin and infected 24 h later with $10^7$ *L. monocytogenes* CFUs. Survival (FIG. 3A) and fecal shedding (FIG. 3B) of *L. monocytogenes* were monitored over time (means+SD are shown, n=1 O per group, from 2 independent experiments).

The kinetics of luminal clearance of *L. monocytogenes* were similar in WT and Rag-/- mice, indicating that B and T lymphocytes of the adaptive immune system do not contribute to pathogen elimination between days 1 and 6 (FIGS. 3A and 3B). Some Rag-/- mice continued to excrete *L. monocytogenes* in their feces 10 days following inoculation, possibly due to defective CD8+ T cell-mediated clearance of systemic infection. (FIG. 3B).

Figure 1C:
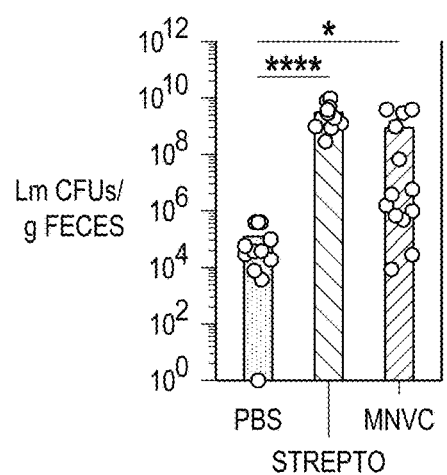
FIG. 1C is a graph of the *L. monocytogenes* (Lm) burden in feces of mice treated with either streptomycin, or a combination of metronidazole, neomycin, vancomycin and clindamycin (MNVC)
Figure 1D:
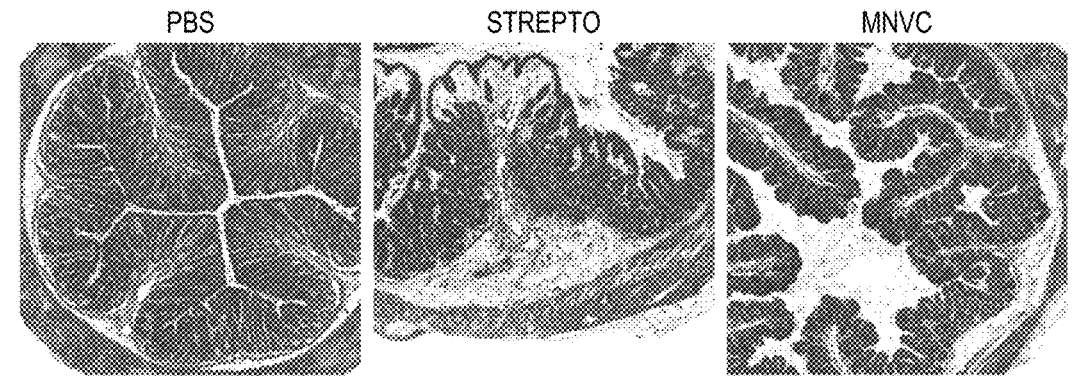
FIG. 1D is a set of micrographs showing representative H&E staining of colonic tissue from mice treated as in FIG. 1C.
Figure 1E:
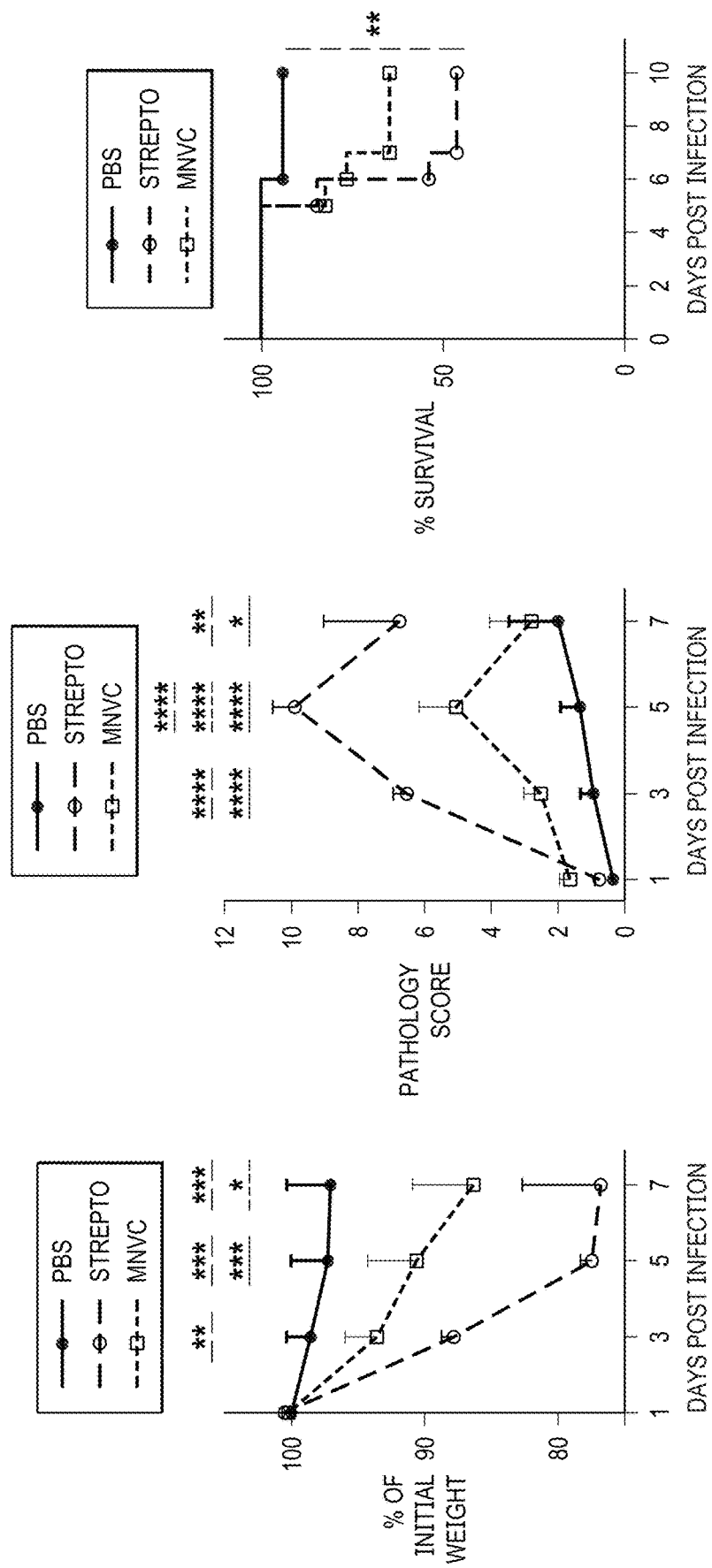
FIG. 1E is a set of graphs presenting data regarding weight loss, pathology score and survival of mice treated as in FIG. 1C.

FIG. 1C shows the Lm burden 1 day post infection with $10^8$ Lm CFUs in feces of mice treated with either streptomycin, or a combination of metronidazole, neomycin, vancomycin and clindamycin (MNVC). Antibiotic treatment was terminated 1 day before infection in all cases (n=9-13, statistics: Kruskal-Wallis test with Dunn's multiple comparison correction). FIG. 1D shows representative H&E staining of colonic tissue from mice treated as in FIG. 1C, 3 days post infection. Arrows indicate edema and stars cellular infiltration. Scale bar=200 μm. FIG. 1E shows data regarding weight loss, pathology score and survival of mice treated as in FIG. 1C. (n=13-17 per group, statistics: Two way ANOVA with Tukey's multiple comparison test and Log-Rank (Mantel-Cox) for survival. For all tests: **=p<0.0001, *=p<0.001, **=p<0.005, *=p<0.05).

A single dose of streptomycin, which markedly enhances murine susceptibility to *Salmonella* infection, or a cocktail of 4 antibiotics (metronidazole, neomycin, vancomycin and clindamycin (MNVC)), also resulted in robust expansion of *L. monocytogenes* (FIG. 1C) and increased morbidity (FIGS. 1D-1E). At day 3 post-infection, edema, inflammatory cell infiltration and epithelial cell shedding were detected in the intestinal tissue of infected, antibiotic- but not PBS-treated mice (FIG. 1D).

Weight loss, the combined pathology score and mortality were consistently increased in antibiotic-treated mice. Treatment of mice with streptomycin induced the highest level of susceptibility, potentially because *L. monocytogenes* 10403s, the strain used in these examples, is highly resistant to this antibiotic, while residual neomycin, vancomycin and clindamycin might inhibit *L. monocytogenes*. (See antibiotic-sensitivity profile of *L. monocytogenes* 10403s in FIG. 4, in which *L. monocytogenes* 10403s was inoculated into medium containing the indicated concentrations of the antibiotics of interest, and incubated at 37° C. overnight, then OD was measured after approximately 12 h.).

High bacterial loads were detected in the spleen and liver of antibiotic-treated mice (results not shown), indicating that antibiotic-mediated compromise of the microbiota predisposes to severe, disseminated *L. monocytogenes* infection, by enabling pathogen expansion in the intestinal lumen and increasing penetration into the intestinal tissue and the systemic circulation.

Example 2: Small Inocula or Gut-Resident *L. monocytogenes* can Promote Infection Upon Dysbiosis In FIG. 5A, WT mice were treated with one dose of oral streptomycin or PBS and infected 24 h later with $10^4$ or $10^2$ (only streptomycin group) CFUs of *L. monocytogenes*. Lm fecal shedding is shown over time (n=8 per group, from two independent experiments). FIG. 5B presents data for weight loss in the animals of FIG. 5A (n=7-8, n=3 for streptomycin-only group, from two independent experiments. Statistics: Two Way ANOVA with Tukey's multiple comparisons; **=p<0.0001, *=p<0.001, **=p<0.005, *=p<0.05).

Figure 5A:
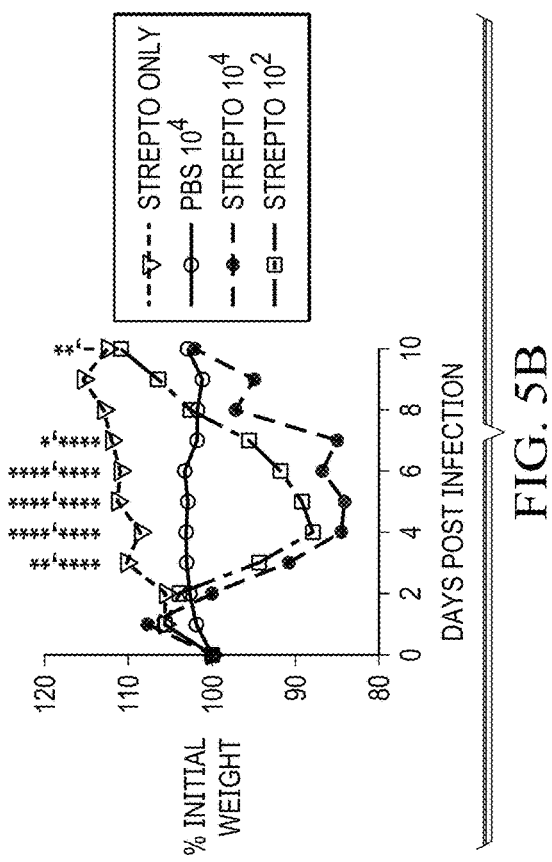
FIG. 5A is a graph of fecal *L. monocytogenes* in antibiotic-treated mice.
Figure 5B:
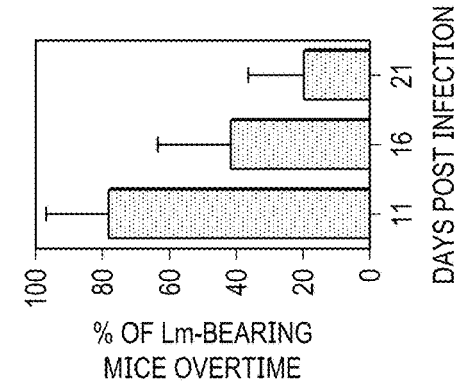
FIG. 5B is a graph of weight over time in the mice of infected with *L. monocytogenes;*

Inoculation of mice with as few as $10^2$ CFUs (~10-7*LD50) following streptomycin-treatment resulted in high-density colonization of the intestinal lumen with weight loss, signs of distress, and diarrhea and fecal shedding persisting for over ten days (FIGS. 5A-5B and data not shown).

FIG. 5C shows the Lm burden in the depicted compartments at d3 post infection for mice treated as in FIG. 5A (n=6, from two independent experiments, Kruskal-Wallis test with Dunn's multiple comparisons). Despite the low inoculum size, *L. monocytogenes* penetrated the epithelium, infiltrated mesenteric lymph nodes and spread to spleen and liver in antibiotic treated, but not PBS treated mice.

Figure 5D:
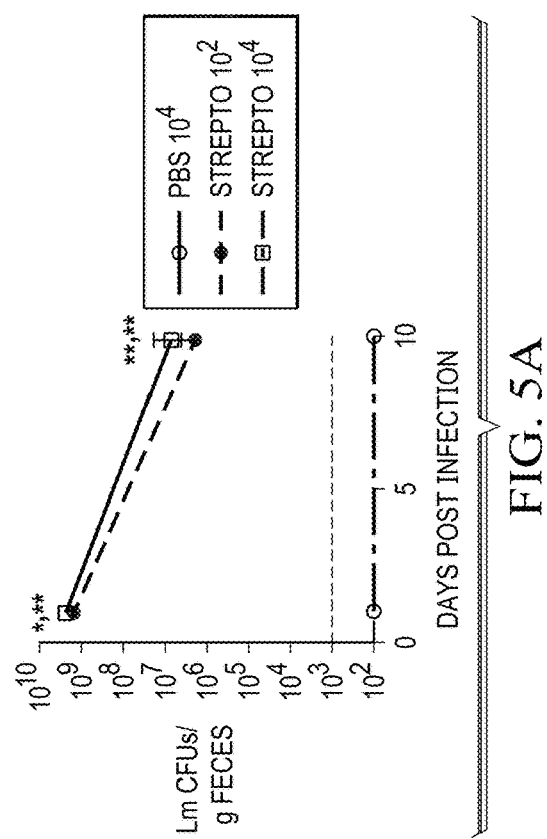
FIG. 5D is a graph of *L. monocytogenes* burden in mice after they became negative for *L. monocytogenes* fecal culture.

These results indicate that microbiota-mediated colonization resistance against *L. monocytogenes* is a major contributor to the high level of murine resistance to oral infection. Roughly 0.5-5% of the human population transiently and asymptomatically carry low levels *L. monocytogenes* in the gastrointestinal tract. To determine whether antibiotic-mediated microbiota depletion in mice with low-level *L. monocytogenes* colonization of the gut could lead to blooming of *L. monocytogenes*, mice were orally infected and fecal pellets were cultured daily until *L. monocytogenes* was undetectable (detection limit=100 CFUs/g feces). Mice infected with $10^8$ *L. monocytogenes* particles were euthanized 1 day following negative fecal cultures for Lm, and whole organs/intestinal contents were homogenized and plated for Lm detection in FIG. 5D (n=6, shown are only mice for which colonies where detected). Once *L. monocytogenes* became undetectable in feces, it could not be cultured from intestinal and abdominal organs, including the gallbladder, which has been previously suggested to be a reservoir for *L. monocytogenes* in infected BALB/c mice, but not in C57BL/6 mice.

The kinetics of *L. monocytogenes* fecal shedding in mice infected with $10^8$ Lm CFUs. Lm presence in the feces was monitored over time, and mice were administered 1 dose of streptomycin (salmon arrow) on the first day after fecal cultures became negative for Lm (n=4, one representative experiment shown). (FIG. 5E)

Figure 5E:
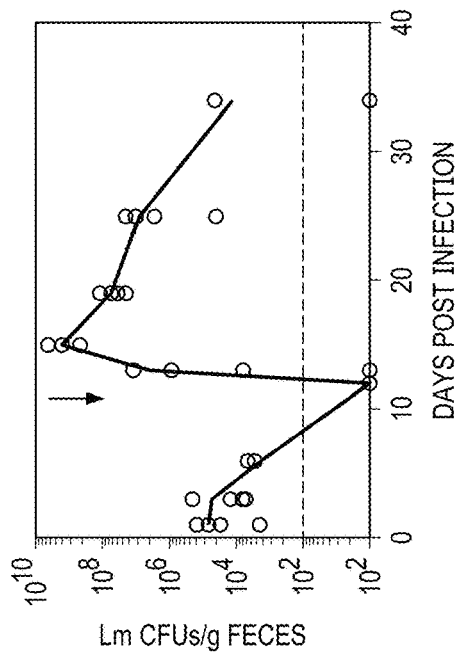
FIG. 5E is a graph of *L. monocytogenes* presence in the feces over time in infected mice.
Figure 5F:
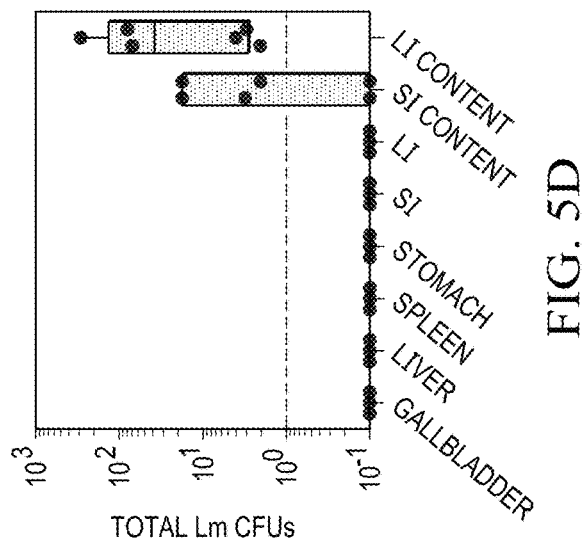
FIG. 5F is a graph of mice with residual *L. monocytogenes* over time.

In FIG. 5F, The percentages of mice still bearing *L. monocytogenes* at the depicted time points post infection was as assessed in FIG. 5E, except that mice were maintained in wire floor cages to prevent coprophagy (n=10 per group, from three different experiments). Administration of streptomycin at different times following infection demonstrated that a high proportion of mice harbor *L. monocytogenes* 11 days (80%), 16 days (40%) and 21 days (20%) post infection, which was longer than previously appreciated. Thus, despite negative fecal cultures, residual *L. monocytogenes* bacteria colonizing a subject can undergo expansion when microbiota-mediated infection resistance is impaired by antibiotic administration.

Example 3: The Gut Microbiota Provides Non-Redundant Protection Against *L. monocytogenes* in Immunocompromised Hosts To investigate the contribution of the microbiota to resistance against oral *L. monocytogenes* infection in immunocompromised hosts, tests were performed in Rag2−/−Il2rg−/− mice (Raggc), which lack T and B cells, as well as NK cells and innate lymphoid cells (ILCs) and are known the be highly susceptible to oral *L. monocytogenes* infection. Rag2−/−Il2rg−/− (Raggc) and WT mice were co-housed for three weeks and infected orally with $10^8$ *L. monocytogenes* CFUs. Survival was monitored over time and results are presented in FIG. 6A (n=3, similar results were obtained with a lower infectious dose). In FIG. 6B, mice of the indicated strain were co-housed for three weeks and then challenged orally with $10^8$ *L. monocytogenes* CFUs. Survival was monitored over time (n=9-15; ****=p<0.0001, *=P<0.05).

These results confirmed that Raggc mice orally inoculated with *L. monocytogenes* doses that are sublethal for WT mice rapidly lost weight and succumbed to infection. Interestingly, although lack of T cells might be assumed to account for marked susceptibility to *L. monocytogenes*, increased susceptibility to oral *L. monocytogenes* infection was only detected in Rag−/−IFNγ−/− double KO mice, and not Rag−/− or Rag−/−IL17−/− mice, suggesting that type 1 ILCs or NK cells, rather than T cells, protect against *L. monocytogenes*.

Figure 7A:
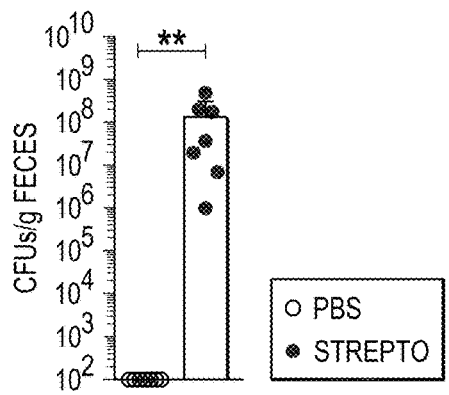
FIG. 7A is a graph of *L. monocytogenes* presence in the feces over time in infected mice treated with antibiotics.
Figure 7B:
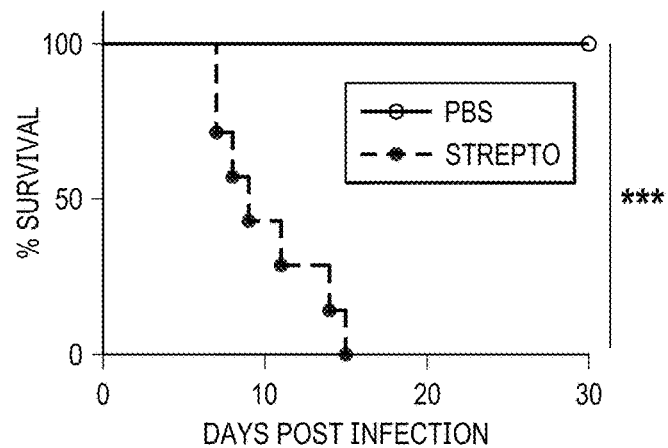
FIG. 7B is a graph of survival of mice infected with *L. monocytogenes* and administered antibiotics.
Figure 7C:
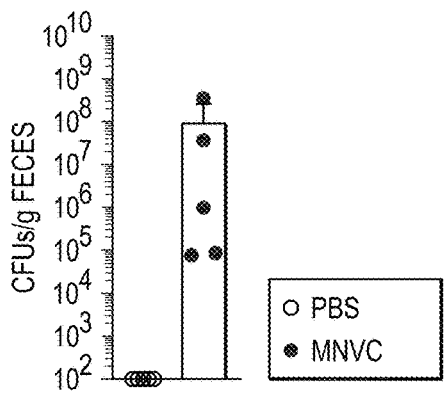
FIG. 7C is a graph of *L. monocytogenes* presence in the feces over time in infected mice treated with antibiotics.
Figure 7D:
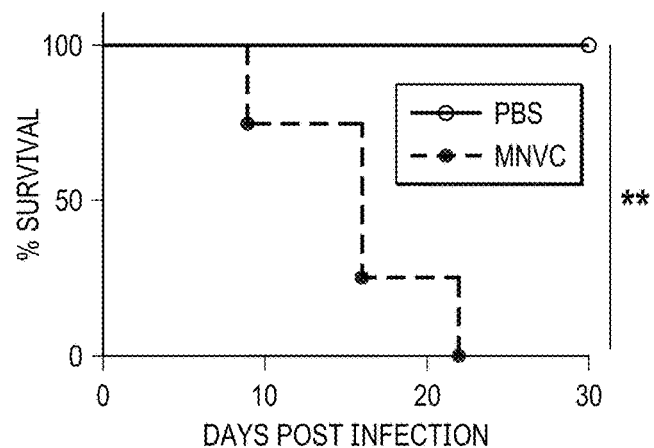
FIG. 7D is a graph of survival of mice infected with *L. monocytogenes* and administered antibiotics.

To determine the role of the microbiota in immunocompromised, highly susceptible mice, Raggc mice were treated with PBS or antibiotics (streptomycin or MNVC) and infected orally 24 h later with a sublethal amount of *L. monocytogenes* ($10^4$ *L. monocytogenes* CFUs). Results are presented in FIG. 7. FIGS. 7A and 7C show *L. monocytogenes* CFUs in feces 1 day post infection (mean±SD). FIGS. 7B and 7D show survival rates. (n=6-7 for (A,B), n=4 for (C,D), from three and two independent experiments respectively; statistics: Mann-Withney test and Log-Rank (Mantel-Cox) test, =p<0.01, *=p<0.001.)

All antibiotic-treated mice succumbed to infection, while all PBS-treated Raggc mice survived (FIGS. 7B and 7D). This indicates that the intestinal microbiota in immunocompromised hosts provides nonredundant, first line defense against *L. monocytogenes* infection.

Example 4: Anti-Cancer Chemotherapy and Antibiotics Synergize in Predisposing the Host to Listeriosis Cancer patients have the highest incidence of severe *L. monocytogenes* infection, with some types of cancer resulting in 1,000 fold increased infection rates. Although the immune-suppressive effects of cancer chemotherapy and radiation therapy might contribute to enhanced susceptibility, experimental evidence for their impact on *L. monocytogenes* infection is lacking. Furthermore, cancer chemotherapy alters the gut microbiota, which may increase susceptibility to infections. A review of patients admitted to MSKCC with a diagnosis of *L. monocytogenes* infection in the past 20 years demonstrated that the majority had been treated with multiple chemotherapeutic agents, corticosteroids or antibiotics.

To determine whether chemotherapy can predispose to *L. monocytogenes* dissemination following oral infection, C57BL/6 mice were treated with doxorubicin and cyclophosphamide, a commonly used chemotherapy combination for a variety of tumors, and subsequently infected with *L. monocytogenes*.

Figure 8A:
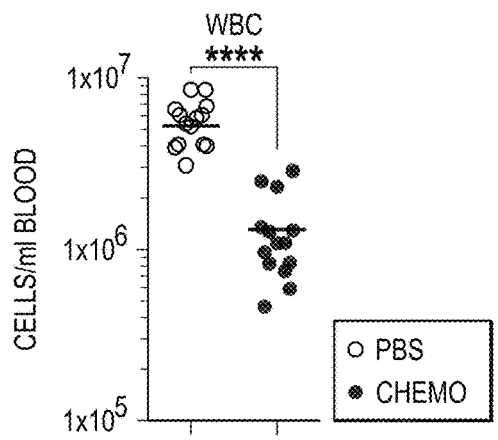
FIG. 8A is a graph of white blood cell count in mice administered chemotherapy.
Figure 8B:
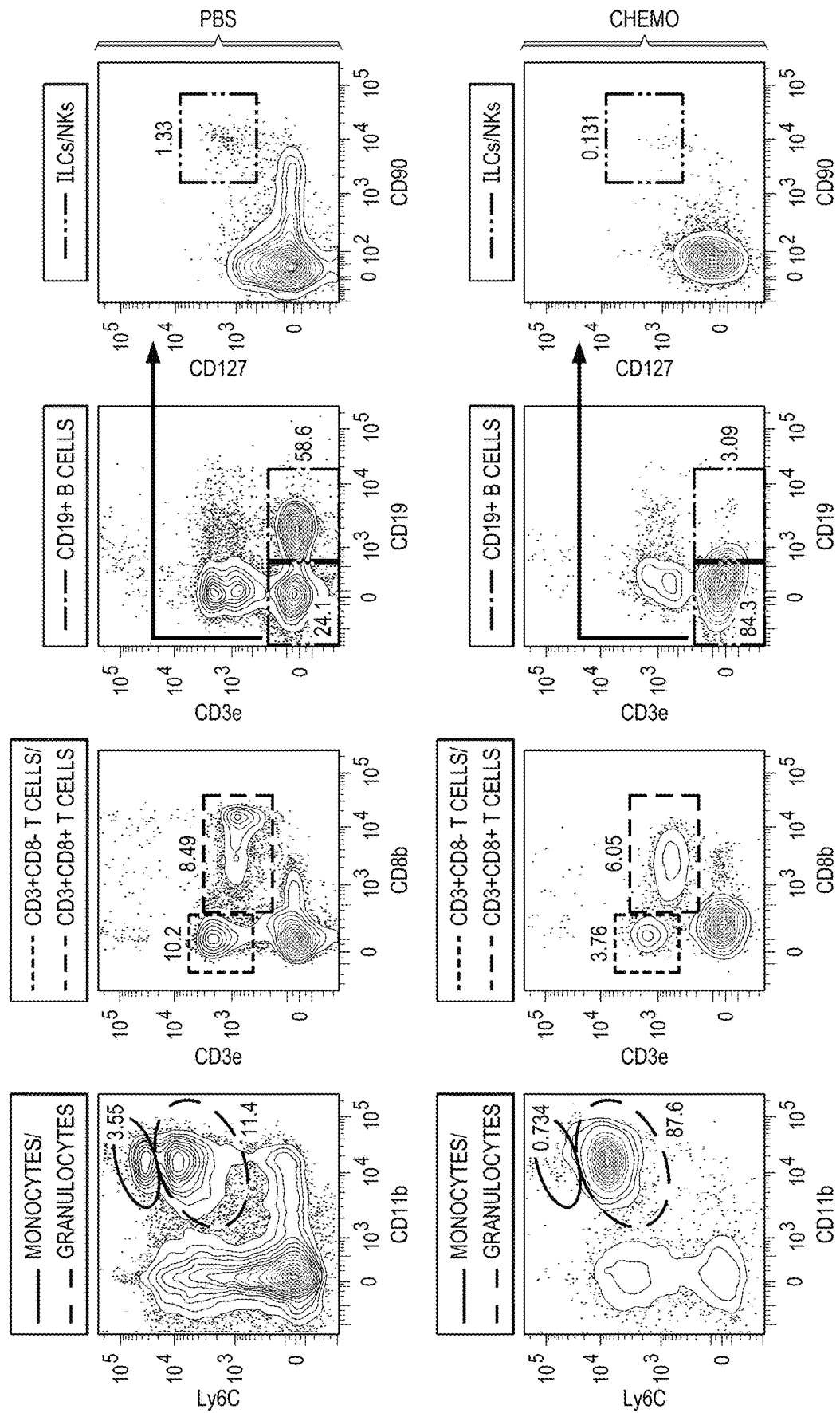
FIG. 8B is a set of representative FACS plots of cells obtained from the mice administered chemotherapy and stained for markers of interest.
Figure 8C:
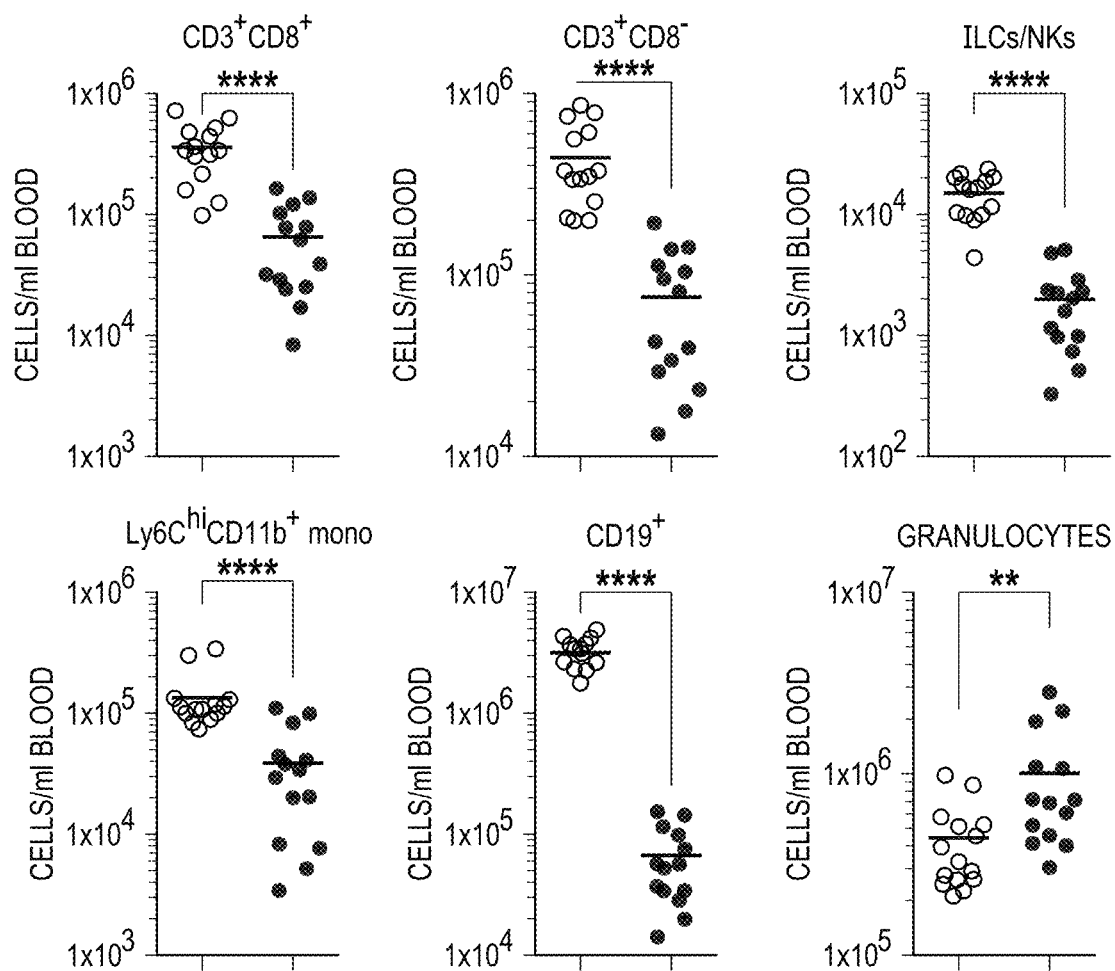
FIG. 8C is a set of graphs graph of cell number of various circulating lymphocytes in mice administered chemotherapy.

To obtain the results in FIG. 8A, mice were administered combined chemotherapy (CHEMO) composed of cyclophosphamide and doxorubicin, or PBS, injected twice i.p. (on day 0 and day 7). On day 8 mice were bled and the white blood cell (WBC) count was determined (n=14). FIG. 8B is a set of representative FACS plots of cells obtained from the mice as in FIG. 8A and stained for markers of interest. FIG. 8C presents cell numbers for circulating leukocytes identified as in (FIG. 8B) from mice shown in (FIG. 8A) (n=14, bars represent means). Chemotherapy reduced the total number of circulating cells approximately 4-fold, with decreased circulating B cells, CD8+ and CD8− T cells, ILCs/NKs, and monocytes (FIGS. 8A-8C).

Figure 8D:
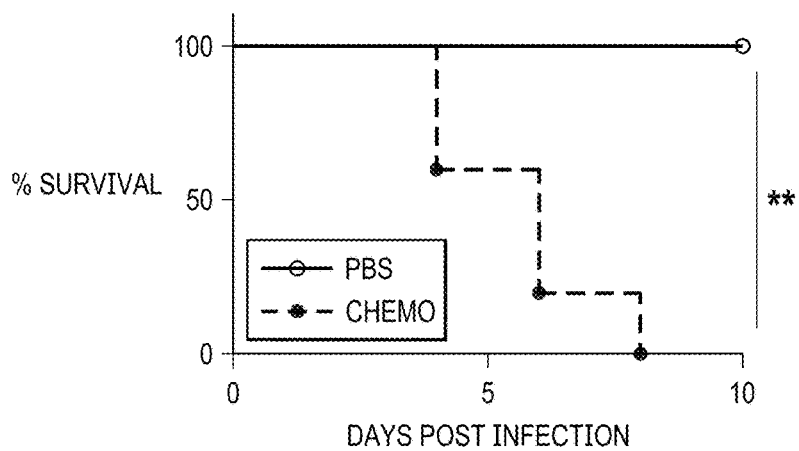
FIG. 8D is a graph of survival of mice administered chemotherapy and infected with *L. monocytogenes*.

Survival of PBS- vs CHEMO-treated mice infected 1 day after the second chemotherapy treatment (d8) with $10^6$ *L. monocytogenes* CFUs is presented in FIG. 8D. Severity of *L. monocytogenes* infection was markedly augmented by chemotherapy administration, with increased morbidity over a range of inoculum doses (not shown), and 100% mortality (FIG. 8D).

Figure 8E:
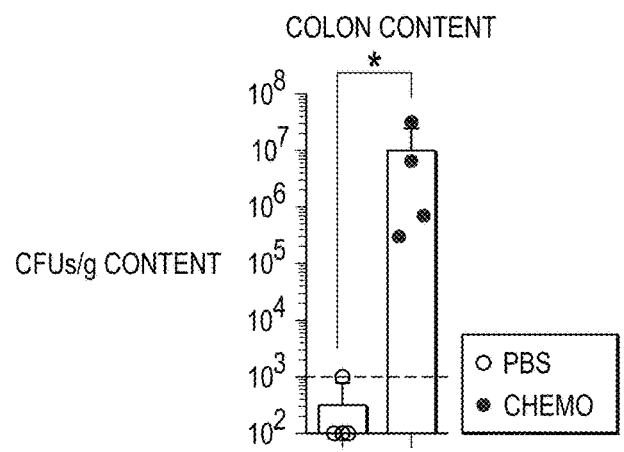
FIG. 8E is a graph of *L. monocytogenes* in colon content in mice administered chemotherapy.

*L. monocytogenes* burden in the colonic content of mice treated and infected as in FIG. 8D with $10^8$ *L. monocytogenes* CFUs, 1 day post infection, is shown in FIG. 8E. One representative of two experiments is illustrated (n=4). Chemotherapy administration resulted in higher *L. monocytogenes* CFUs in the large intestine lumen 24 h post infection (FIG. 8E), suggesting that drug-induced dysbiosis or inflammation facilitates *L. monocytogenes* growth, contributing to greater dissemination.

Figure 8F:
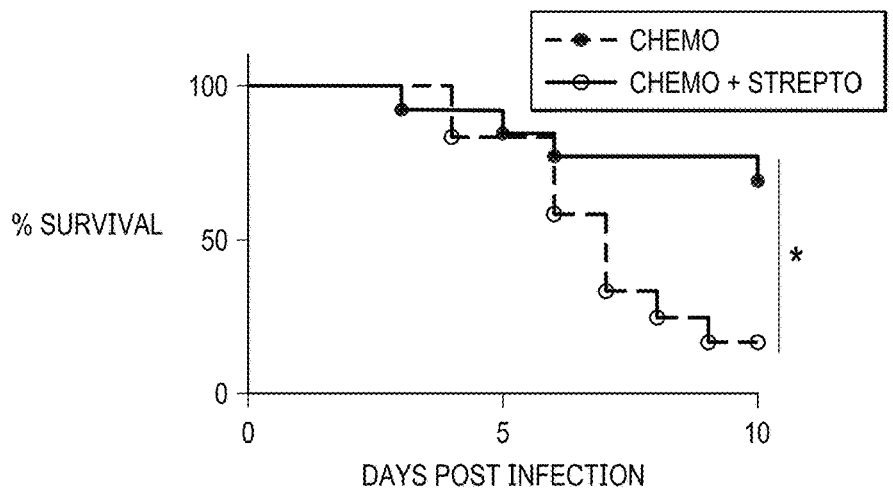
FIG. 8F is a graph of survival of mice administered chemotherapy and antibiotics and infected with *L. monocytogenes*.

Cyclophosphamide treatment has been shown to reduce the abundance of bacterial strains belonging to the order Clostridiales in a mouse model (Viaud S, Saccheri F, Mignot G, Yamazaki T, Daillere R, Hannani D, Enot D P, Pfirschke C, Engblom C, Pittet M J, et al. The intestinal microbiota modulates the anticancer immune effects of cyclophosphamide. Science. 2013; 342(6161):971-6). To determine whether antibiotic-induced microbiota perturbation increases susceptibility of chemotherapy treated mice to oral *L. monocytogenes* infection, chemotherapy recipients were treated with streptomycin or PBS prior to infection with a low *L. monocytogenes* inoculum. Specifically, mice were treated as in FIG. 8A, administered either PBS or streptomycin on day 7 (concomitant with the second CHEMO administration) and infected 24 h later with $10^4$ Lm CFUs (n=12-13; statistics: Mann-Whitney test in A, C, E, Log-Rank test in D, F. **=p<0.0001, =p<0.005, *=p<0.05). In concordance with results obtained in Ragge mice, streptomycin treatment accentuated chemotherapy-induced susceptibility and resulted in increased mortality rates (FIG. 8F).

Chemotherapy likely enhanced susceptibility to *L. monocytogenes* infection by reducing immune cells in the circulation, particularly inflammatory monocytes as well as interferon gamma producing ILCs/NKs, whose defensive role in *L. monocytogenes* infection remains an object of debate. In the absence of such cell types, the microbiota provided a parallel line of defense, which directly acted on *L. monocytogenes*, reducing its growth. Antibiotic treatment destroyed this defense mechanism, thus exposing the host to infection even with extremely low *L. monocytogenes* doses.

Chemotherapy administration per se resulted in a significantly higher *L. monocytogenes* burden in the large intestinal lumen 1 day post infection, suggesting that microbiota perturbation or inflammatory conditions induced by chemotherapeutics might also contribute to the enhanced susceptibility of cancer patients.

Example 5: Commensal Microbes Efficiently Antagonize *L. monocytogenes* Ex Vivo

Antibiotic-mediated depletion of commensals can reduce mucosal and systemic immune defenses and commensal-driven, MyD88-mediated stimuli induce RegIIIγ production by the intestinal epithelium and reduce *L. monocytogenes* growth in the small intestine. On the other hand, intestinal commensal bacteria can also directly inhibit pathogens by competing for nutrients or by producing bacteriocins.

To initially investigate how the intestinal microbiota inhibits in vivo *L. monocytogenes* expansion, ex vivo experiments were performed to assess if commensals, in the absence of host derived factors, mediate *L. monocytogenes* clearance.

Content from small or large intestine was harvested from WT mice, re-suspended in reduced PBS and inoculated with increasing doses of *L. monocytogenes* in either anaerobic or aerobic conditions. In particular, content from small and large intestine was collected from WT mice and resuspended in reduced PBS. *L. monocytogenes* (Lm) was inoculated at the depicted doses (FIG. 9A) in 100 μl of intestinal suspension and cultured in anaerobic (upper panels) or aerobic (lower panels) conditions. Lm CFUs were enumerated over time by plating (n=3 mice per time point, one representative of two experiments shown, circles represent individual values, lines represent medians). Intestinal contents killed *L. monocytogenes* within 24 h, with small intestinal content demonstrating greater activity at reducing *L. monocytogenes* CFUs (FIG. 9A).

Large intestinal contents had more variable inhibitory activity, but in all cases reduced viable CFUs over 24 h. $10^3$ Lm CFUs were inoculated in intestinal contents prepared as in (FIG. 9A) or in sterile filtered aliquots of the same (n=3 mice per time point, one representative of two experiments shown) and grown aerobically for the depicted times (FIG. 9B). *L. monocytogenes* grew exponentially in intestinal content that had been filtered and cleared of bacteria, indicating that neither lack of nutrients in the initial suspension nor presence of antimicrobial molecules of host origin account for the bactericidal effect of intestinal contents (FIG. 9B).

Figure 9A:
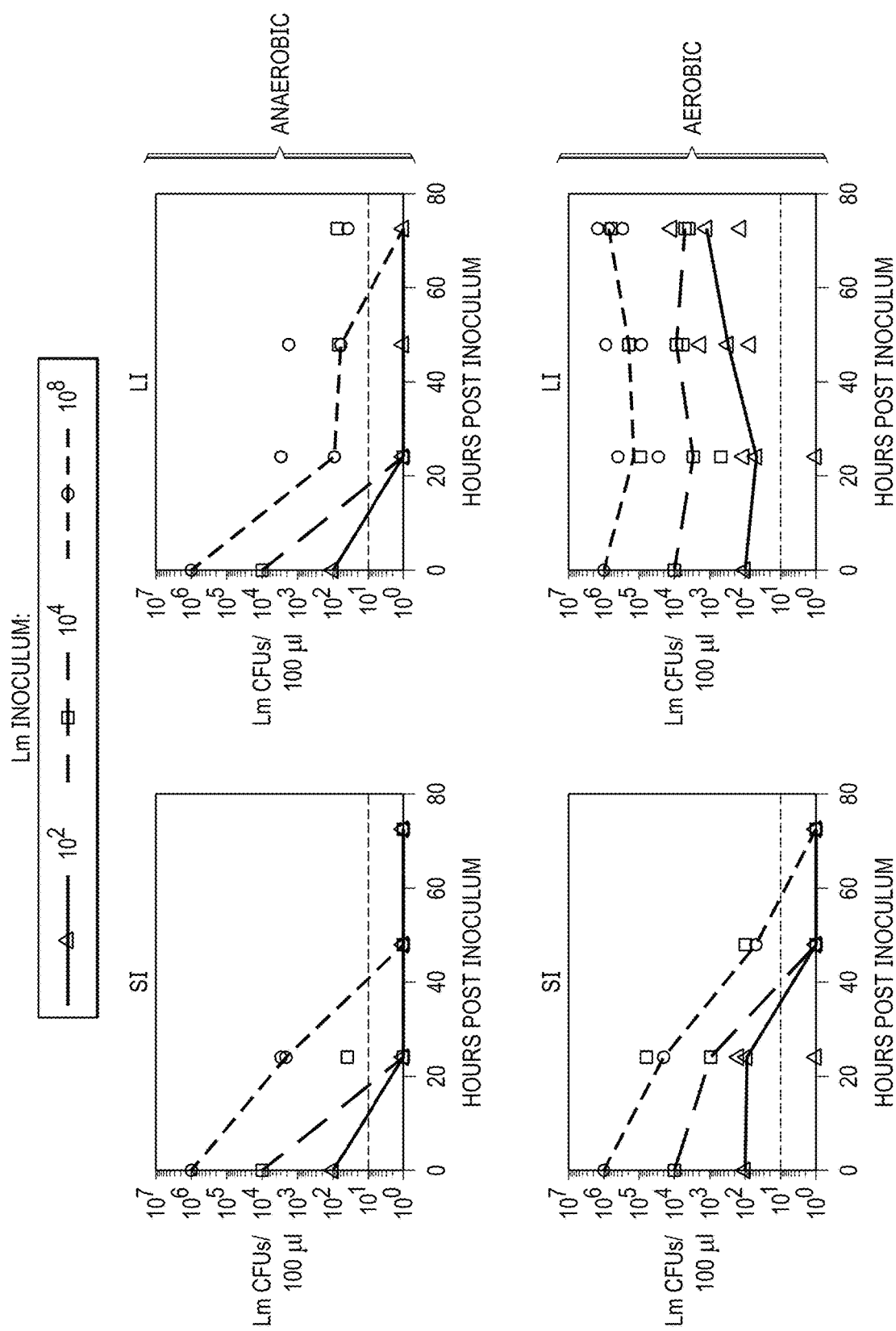
FIG. 9A is a set of graphs depicting growth of *L. monocytogenes* in intestinal suspensions and cultured in anaerobic (upper panels) or aerobic (lower panels) conditions.

Exposure of ex vivo cultures to oxygen delayed *L. monocytogenes* clearance from small intestine content, and abolished clearance from large intestine content (FIG. 9A). These results suggest that obligate anaerobic bacteria inhibit and possibly kill *L. monocytogenes*.

Figure 9B:
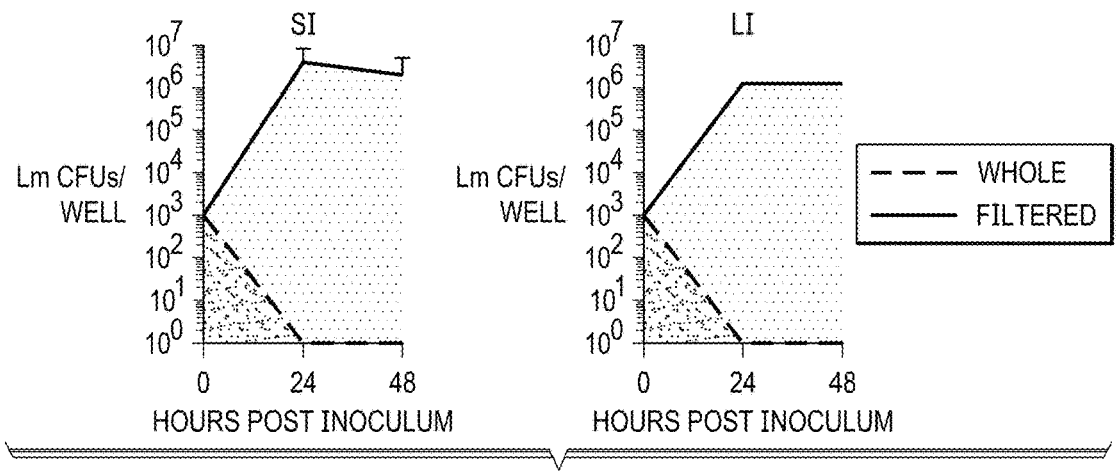
FIG. 9B is a set of graphs depicting *L. monocytogenes* growth in filtered or unfiltered intestinal suspensions from the large intestine or small intestine.
Figure 9C:
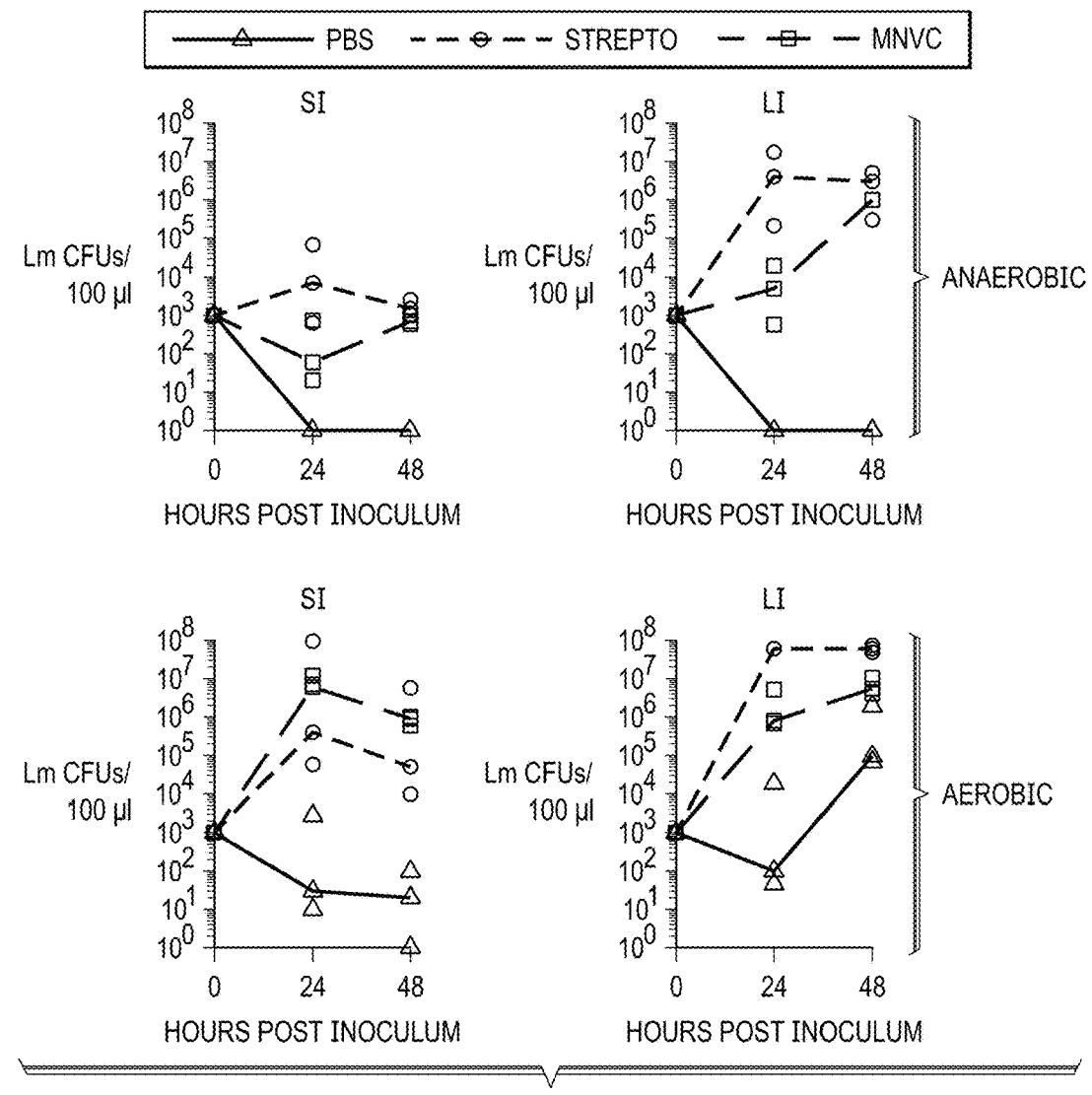
FIG. 9C is a set of graphs of depicting growth of *L. monocytogenes* in intestinal suspensions and cultured in anaerobic (upper panels) or aerobic (lower panels) conditions in the presence of antibiotics.

In FIG. 9C, mice were treated in the same experimental setup as in FIG. 9A, except that intestinal content was collected from PBS, streptomycin or MNVC-treated mice one day after termination of treatment (n=3 mice per time point, one representative of two experiments shown, circles represent individual values, lines represent medians). Intestinal content from mice that had been previously treated with antibiotics lost the capacity to eliminate *L. monocytogenes*, enabling survival (small intestine) or expansion (large intestine) of the pathogen (FIG. 9C). Exposure to oxygen synergized with the effect of antibiotic treatment decreasing the capacity of commensals to antagonize *L. monocytogenes* (FIG. 9C). This shows that the enhanced infection and delayed *L. monocytogenes* clearance in antibiotic-treated mice depended upon direct effects on microbiota composition, rather than on indirect consequences on the immune system.

Figure 9D:
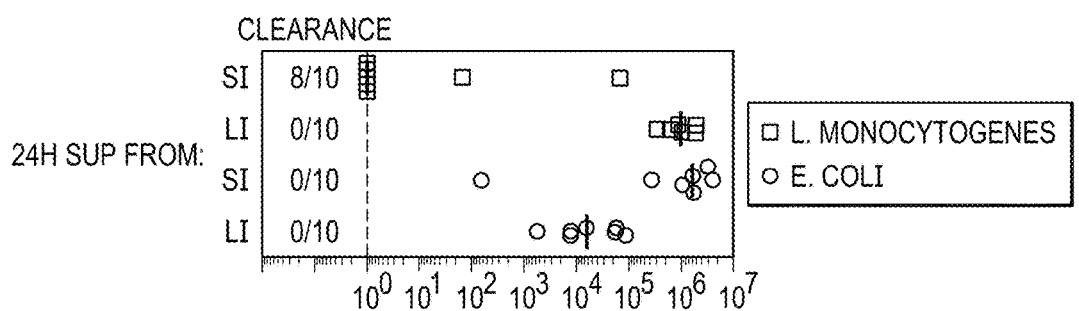
FIG. 9D is a graph of growth of either *L. monocytogenes* or *E. coli* DH5-α in inoculated in sterile-filtered supernatants from intestinal cultures when grown aerobically.

To investigate the inhibitory mechanisms operating in the experiments of FIGS. 9A-9C, contents from small or large intestine were co-cultured with $10^3$ Lm CFUs for 24 h, a time sufficient to allow inhibitory mechanisms to take place, and the resulting culture supernatants were sterile filtered (24 h-sup). In FIG. 9D, $10^3$ CFUs of either *L. monocytogenes* or *E. coli* DH5-α were inoculated in sterile-filtered supernatants and grown aerobically for 24 h (n=10 from different mice and three independent experiments).

24 h-sups from large intestinal contents promoted growth of both *L. monocytogenes* and *E. coli*, but *L. monocytogenes* was completely eliminated from 8 out of 10 small intestinal 24 h-sups. By contrast, *E. coli* grew exponentially in filtered supernatants, suggesting that different mechanisms interfere with L, *monocytogenes* expansion in the small and large intestine, some of which are selective and discriminate among bacteria.

Overall, these results suggest that bacteria inhabiting different intestinal regions efficiently eliminate *L. monocytogenes* by multiple mechanisms; these might include production of anti-bacterial molecules as well as nutrient competition or contact dependent inhibition.

Example 6: Identification of Intestinal Commensal Bacteria Associated with Protection from *L. monocytogenes* Infection In Vivo To identify intestinal commensal species that provide colonization resistance against *Listeria monocytogenes*, streptomycin (2 mg/mouse, to facilitate microbiota recovery) or MNVC to C57BL/6 were administered to mice, which were then challenged with an oral inoculum of *L. monocytogenes* 1, 5, 16, 21 or 27 days following completion of antibiotic treatment. 3 mice per group were single-housed and infected with $10^8$ Lm CFUs at each of the relevant time points (post antibiotic treatment). Mice were euthanized 24 hours after infection and *L. monocytogenes* was quantified by culture of intestinal contents, liver and spleen. Small intestine, cecum or colon contents were also subjected to 16S rRNA gene sequencing to determine microbiota composition at each time point.

Figure 10B:
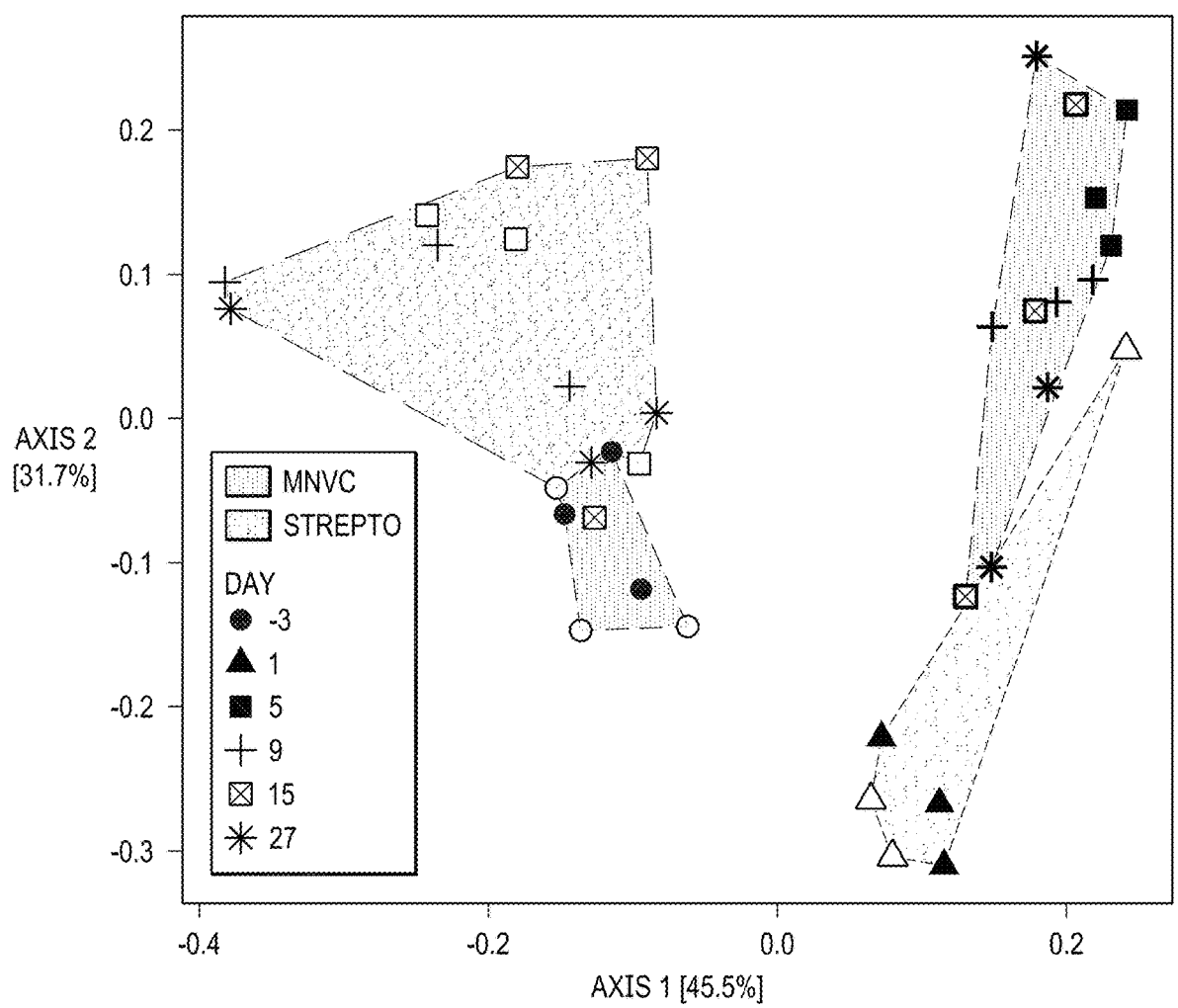
FIG. 10B is a graph of Principle Coordinates Analysis (PCoA) of microbiota 16S sequences from fecal pellets collected from the animals of FIG. 10A on the day of infection with *L. monocytogenes*.
Figure 10A:
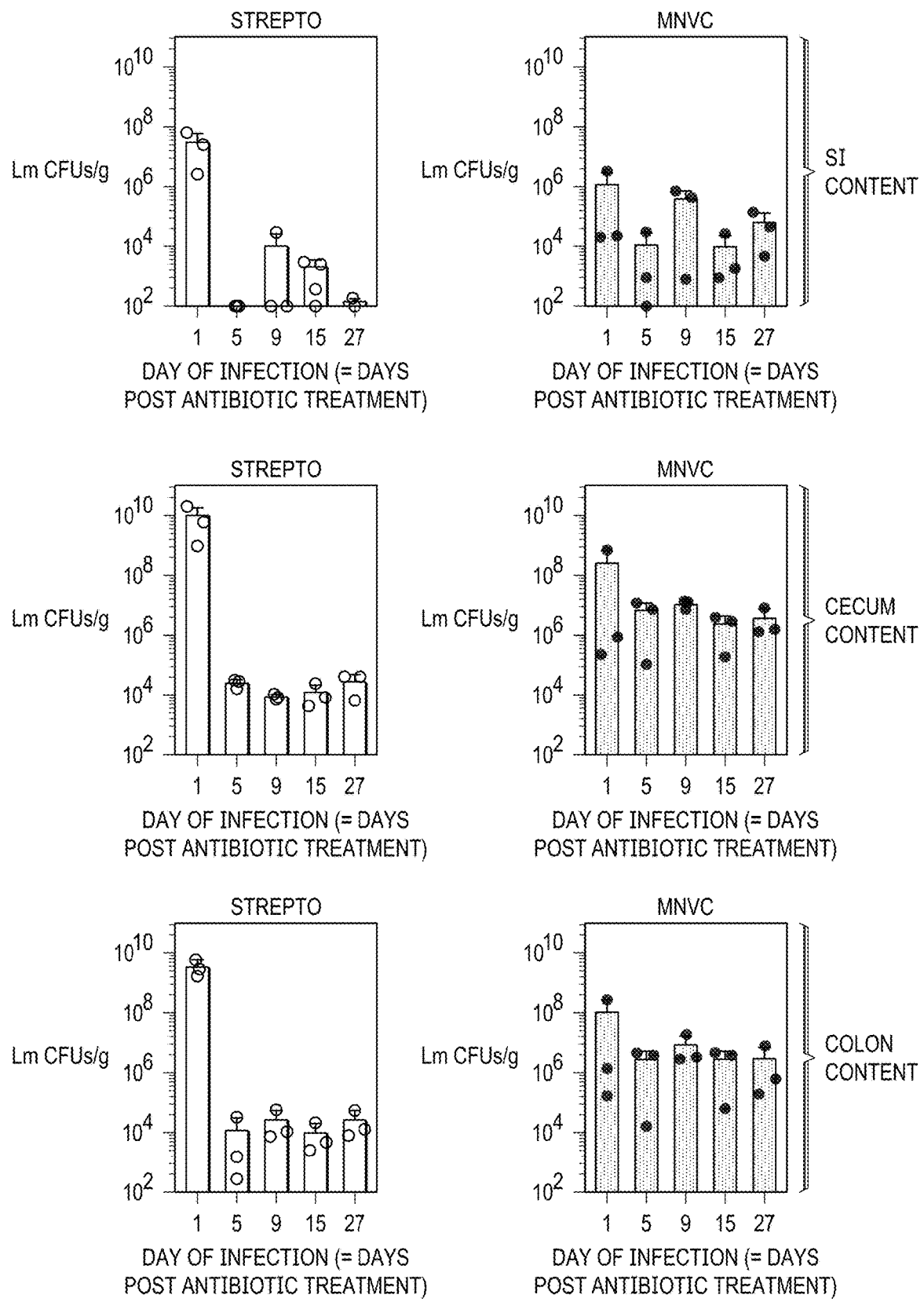
FIG. 10A is a set of graphs showing susceptibility of antibiotic-treated mice to *L. monocytogenes* infection over time.

High susceptibility to infection persisted for only one day following streptomycin treatment and mice fully recovered resistance (i.e. infection levels undistinguishable from PBS-treated animals) within 5 days of streptomycin termination. In contrast, MNVC treatment resulted in susceptibility to *L. monocytogenes* intestinal colonization for up to 27 days following antibiotic cessation, suggesting that some bacterial species crucial for protection were irreversibly ablated (FIG. 10A).

Principle Coordinates Analysis (PCoA) of microbiota 16S sequences from fecal pellets collected from the animals on the day of infection was also performed. Results are presented in FIG. 10B. The colored areas plotted indicate: gray=pre-treatment; green=d1 post antibiotics (any antibiotics); salmon=d5-27 streptomycin; blue=d5-27 MNVC. PCoA of 16S sequences demonstrated that the microbiota of streptomycin-treated mice returned to pre-treatment composition within 5 days, while MNVC-treated animals maintained a distinct microbiota composition (FIG. 10B).

Figure 10C:
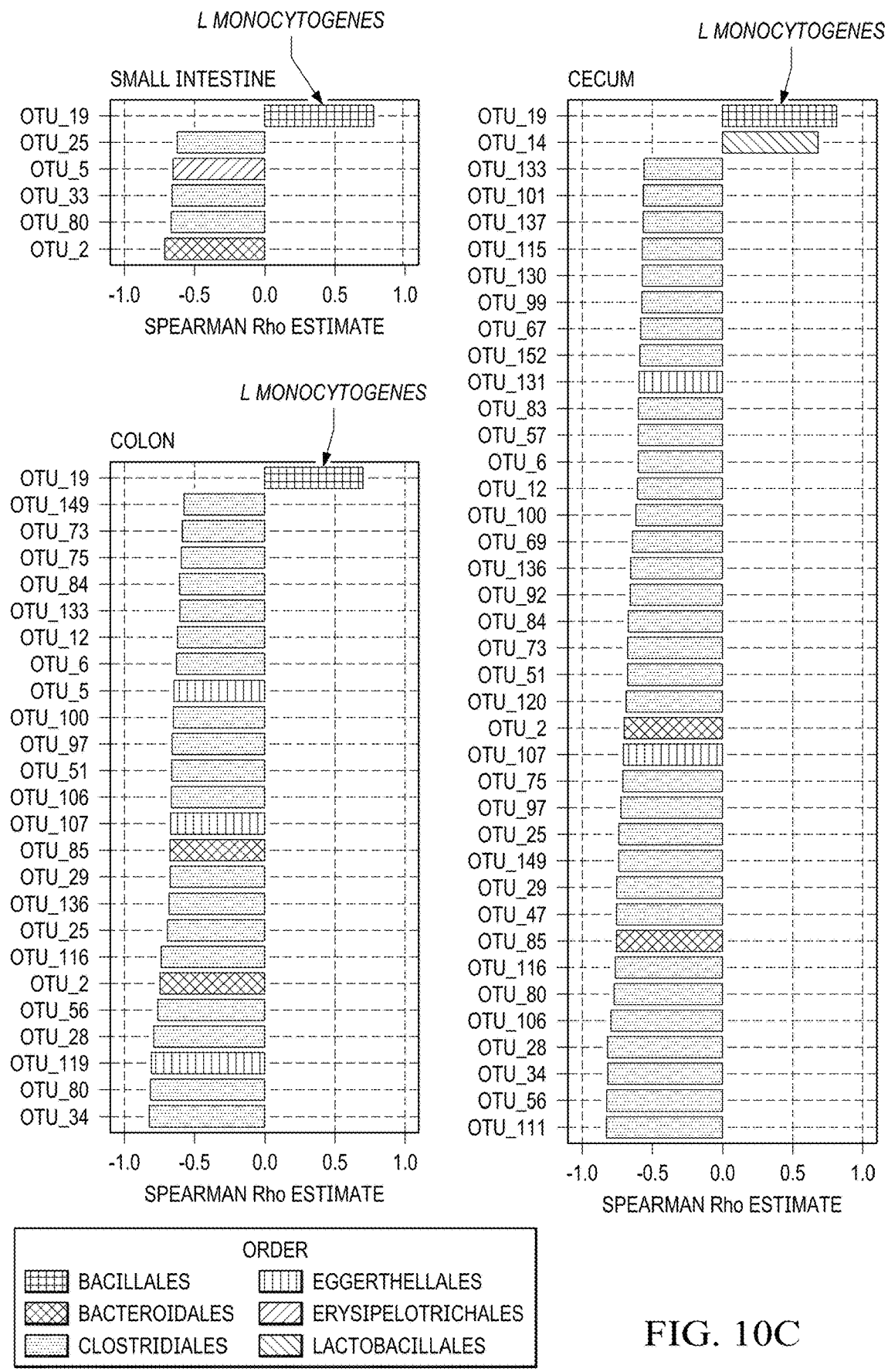
FIG. 10C is graph of the Spearman rank correlation analysis between *L. monocytogenes* susceptibility and bacterial taxa identified by 16S rRNA gene sequencing.
Figure 11:
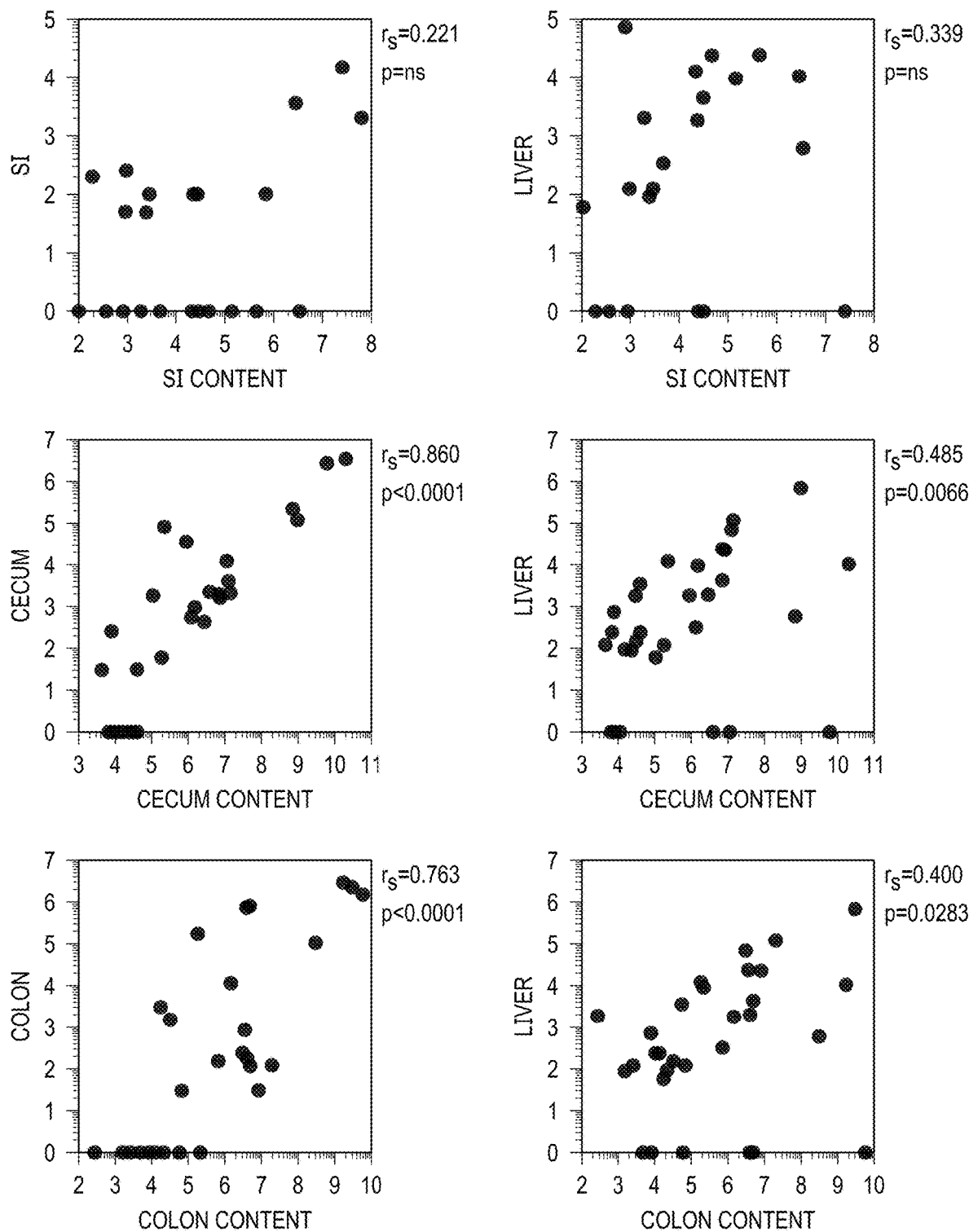
FIG. 11 is a set of graphs of *L. monocytogenes* density in organs of the mice of FIG. 10A.

*L. monocytogenes* density in cecum and colon content correlated with that in cecum and colon wall and the liver (n=6) (FIG. 11). Spearman rank correlation analysis between *L. monocytogenes* susceptibility and bacterial taxa identified by 16S rRNA gene sequencing, as previously described (Ubeda C, Bucci V, Caballero S, Djukovic A, Toussaint N C, Equinda M, Lipuma L, Ling L, Gobourne A, No D, et al. Intestinal microbiota containing Barnesiella species cures vancomycin-resistant *Enterococcus faecium* colonization. Infection and immunity. 2013; 81(3):965-73; Buffie C G, Bucci V, Stein R R, McKenney P T, Ling L, Gobourne A, No D, Liu H, Kinnebrew M, Viale A, et al. Precision microbiome reconstitution restores bile acid mediated resistance to *Clostridium difficile*. Nature. 2015; 517 (7533):205-8), identified several bacterial species significantly associated with protection (FIG. 10C, (Spearman correlation between identified OTUs and *L. monocytogenes* CFUs enumerated by plating 1 day post infection, shown separately for small intestine, cecum and colon content; Shown are only significant hits, BH corrected p value <0.05.)). The majority of taxa belonged to the order Clostridiales (FIG. 10C).

Example 7: Commensal Clostridiales Protect from *L. monocytogenes* Infection Upon In Vivo Transfer To identify specific bacterial strains that can inhibit *L. monocytogenes* growth, a panel of Clostridia strains including human isolates (Atarashi K, Tanoue T, Oshima K, Suda W, Nagano Y, Nishikawa H, Fukuda S, Saito T, Narushima S, Hase K, et al. Treg induction by a rationally selected mixture of Clostridia strains from the human microbiota. Nature. 2013; 500(7461):232-6), commercially available strains and isolates from mouse stool were screened. A commercially available *Lactobacillus gasseri* strain was included as a positive control, as L. gasseri produces at least 3 toxins that target Gram+bacteria, including *L. monocytogenes*. The commensal bacteria were grown anaerobically and inoculated in medium (FIG. 12A) or in autoclaved intestinal content (FIG. 12B) at OD=0.1. 103 *L. monocytogenes* CFUs were added, and *L. monocytogenes* expansion was evaluated after 24 h of anaerobic co-culture (n=3, shown 1 representative of 2-4 experiments per condition). Autoclaved cecal content was prepared by resuspending large intestinal content into PBS at 100 mg/ml and autoclaving the suspension for 21 minutes; the suspension was then incubated in the anaerobic chamber for at least 24 h prior to use.

Figures 12A, 12B:
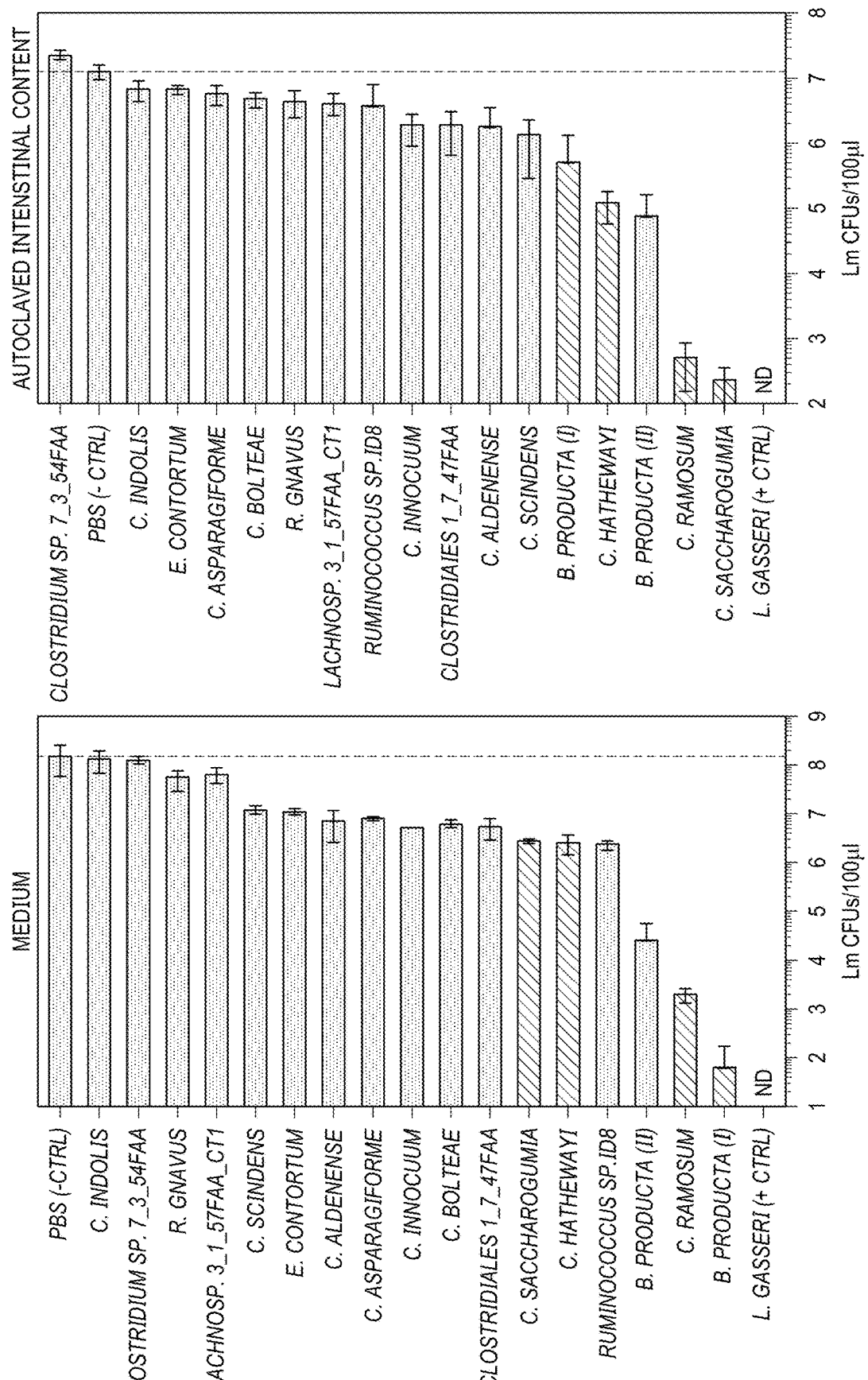
FIG. 12A is a graph of *L. monocytogenes* growth in co-culture under anaerobic conditions with various bacterial strains.
FIG. 12B is a graph of *L. monocytogenes* growth in co-culture with autoclaved cecal content-medium under anaerobic conditions with various bacterial strains.

Co-culture with *L. monocytogenes* under anaerobic conditions demonstrated that several bacterial strains inhibited *L. monocytogenes* growth by over 3 orders of magnitude (FIG. 12A). The bacterial strains also inhibited *L. monocytogenes* growth when added to autoclaved cecal content (FIG. 12B).

Figure 12C:
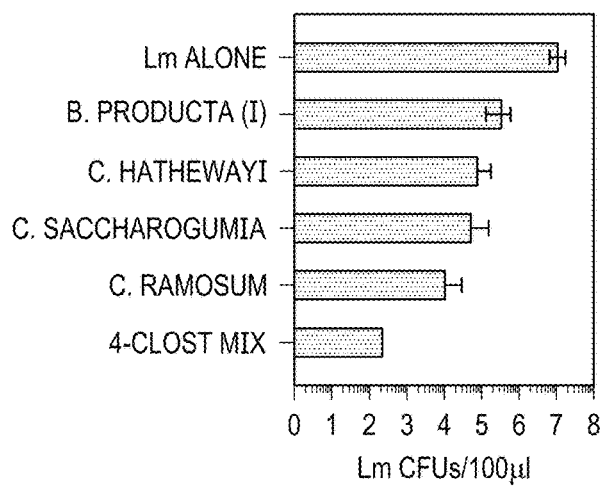
FIG. 12C is a graph of *L. monocytogenes* growth in col-culture with autoclaved cecal content-medium under anaerobic conditions with individual bacterial strains and a mixture of four strains.

Four strains (*C. saccharogumia, C. ramosum, C. hathewayi,* and *B. producta*) were identified that consistently reduced *L. monocytogenes* growth under varied culture conditions and that provided enhanced anti-*L. monocytogenes* properties as a mixture (designated as "4-Clost"). FIG. 12C presents data showing that, although each of these strains inhibited *L. monocytogenes* alone, 4-Clost mix produced markedly more pronounced inhibition (bars represent mean+/−standard deviation).

Figure 12D:
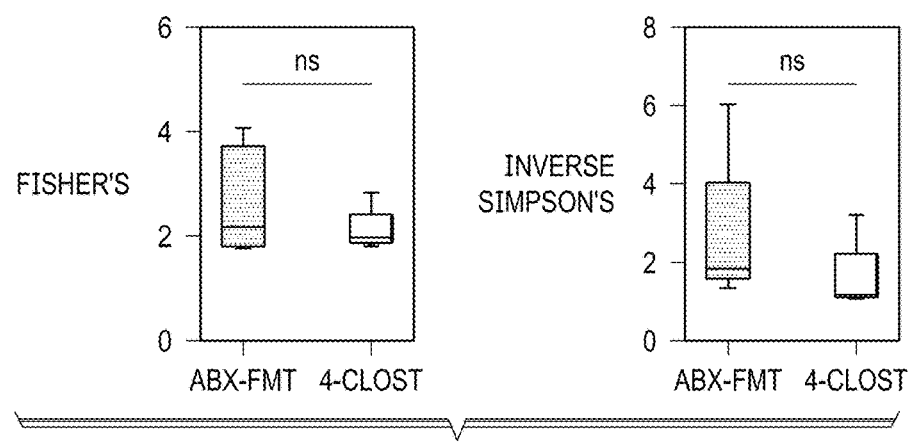
FIG. 12D is a set of graphs of the diversity index of microbiota.

GF mice were reconstituted with the 4-Clost mixture or fecal pellet (ABX-FMT) from MNVC-treated mice via oral gavage. After 10 days mice were challenged with $10^7$ *L. monocytogenes* CFUs. FIG. 12D presents a diversity index of the microbiota 10 days post-reconstitution (=day of *L. monocytogenes* infection) in feces of ex-GF treated as indicated, based on OTU composition as assessed by sequencing of 16s rRNA genes. The *L. monocytogenes* burden in the feces of ex-GF animals was evaluated 24 h post infection, with results presented in FIG. 12E. The mice were then euthanized at day 3 post infection and *L. monocytogenes* CFUs were quantified in intestinal content and depicted organs, with results presented in FIGS. 12F and 12G. (For FIGS. 12D-12F) circles represent individual mice, bars represent median values; n=9 except in (C), n=5; statistics: Mann-Whitney test, *=p<0.05, =p<0.005, *=p<0.001, ****=p<0.0001).

Figure 12E:
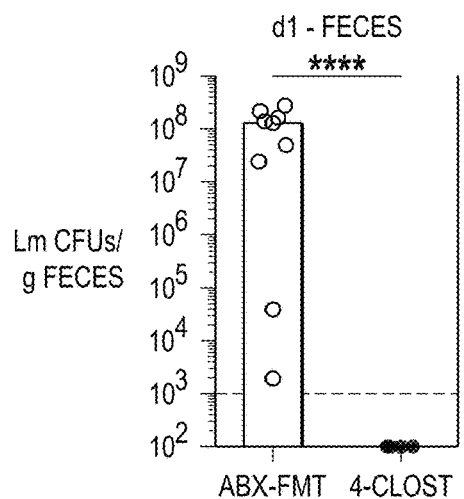
FIG. 12E is a graph of the effects of a mixture of four therapeutic bacteria on fecal *L. monocytogenes* content.
Figure 13A:
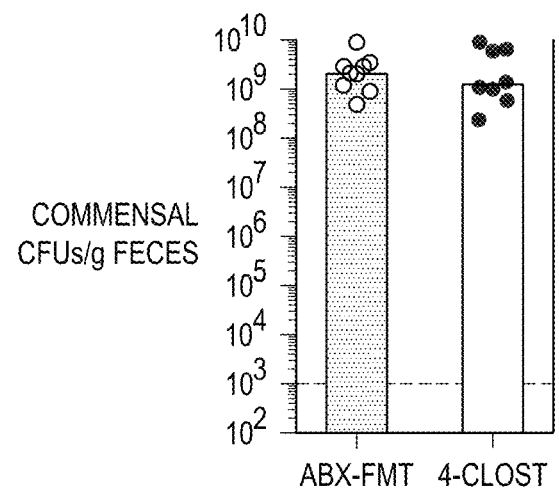
FIG. 13A is a graph of the effects of a mixture of four therapeutic bacteria on commensal bacteria in mice.

Reconstitution levels of ex-GF mice of FIGS. 12D and 12E, as measured by anaerobic plating of fecal pellets 2 days post reconstitution, are presented in FIG. 13A. The density of commensal bacteria was determined by culture. $10^3$ *L. monocytogenes* CFUs were inoculated into resuspended fecal pellets obtained from ex-GF mice described in FIGS. 12D and 12E at day 2 post reconstitution. *L. monocytogenes* expansion was evaluated after 24 h of anaerobic co-culture and results are presented in FIG. 12B. For both FIGS. 13A and 13B, results from individual mice and medians are shown. n=9 mice, Statistics: Mann-Whitney test, **=P<0.005.

Figure 13B:
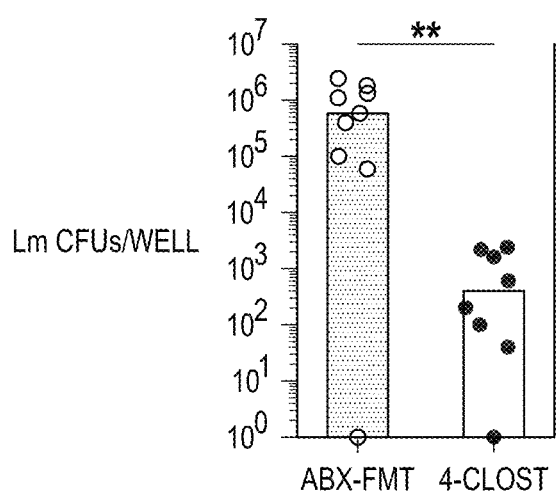
FIG. 13B is a graph of the effects of four therapeutic bacteria on fecal *L. monocytogenes* content.

Mice reconstituted with FMT-ABX or 4-Clost had similar bacterial densities and overall microbiota diversity (FIG. 12D and FIG. 13A). Culture of *L. monocytogenes* in fecal pellets from the two groups demonstrated reduced growth in fecal cultures derived from 4-Clost mice (FIG. 13B).

Figure 12F:
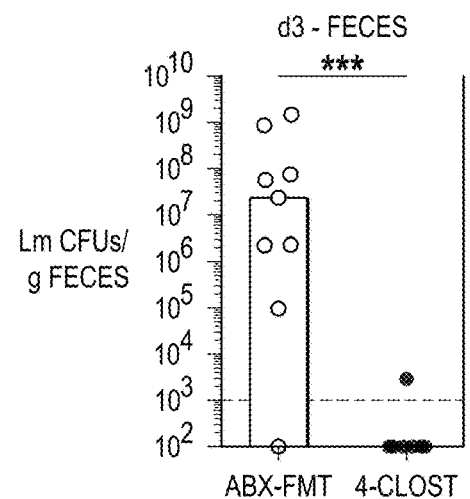
FIG. 12F is a graph of the effects of a mixture of four therapeutic bacteria on fecal *L. monocytogenes* content.
Figure 12G:
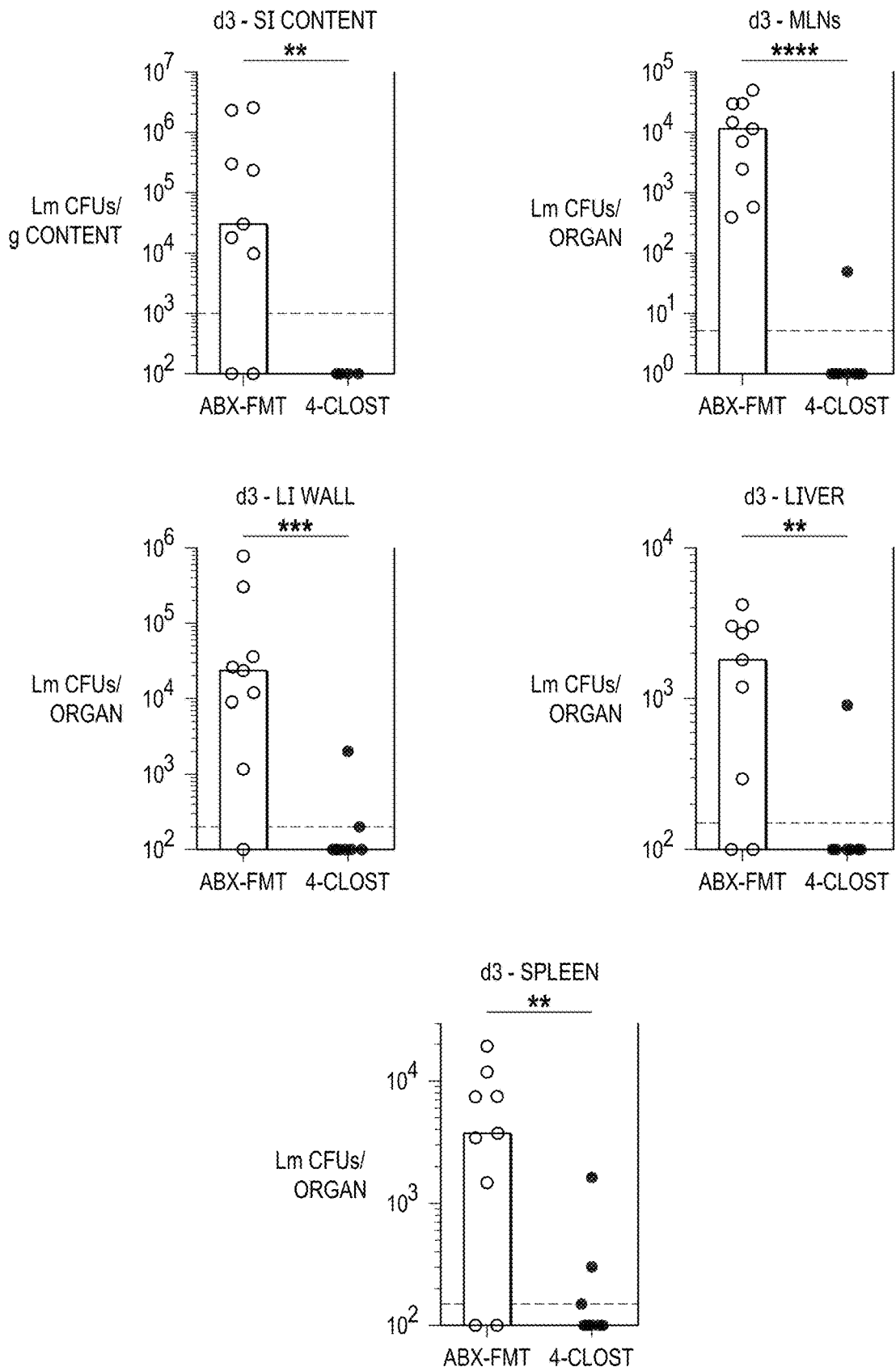
FIG. 12G is a graph of the effects of a mixture of four therapeutic bacteria on *L. monocytogenes* content in various organs.

Mice reconstituted with 4-Clost had markedly lower levels of luminal *L. monocytogenes* as compared to ABX-FMT mice (FIGS. 12E and 12F). Furthermore, while dissemination of *L. monocytogenes* to mesenteric lymph nodes (MLNs), spleen and liver was not detected or was moderate in 4-Clost mice, high-level dissemination was detected in FMT-ABX mice (FIG. 12G). Thus, by reducing *L. monocytogenes* burden in the intestinal lumen, the 4-Clost mixture prevented invasive listeriosis and systemic spread of the pathogen.

Figure 13C:
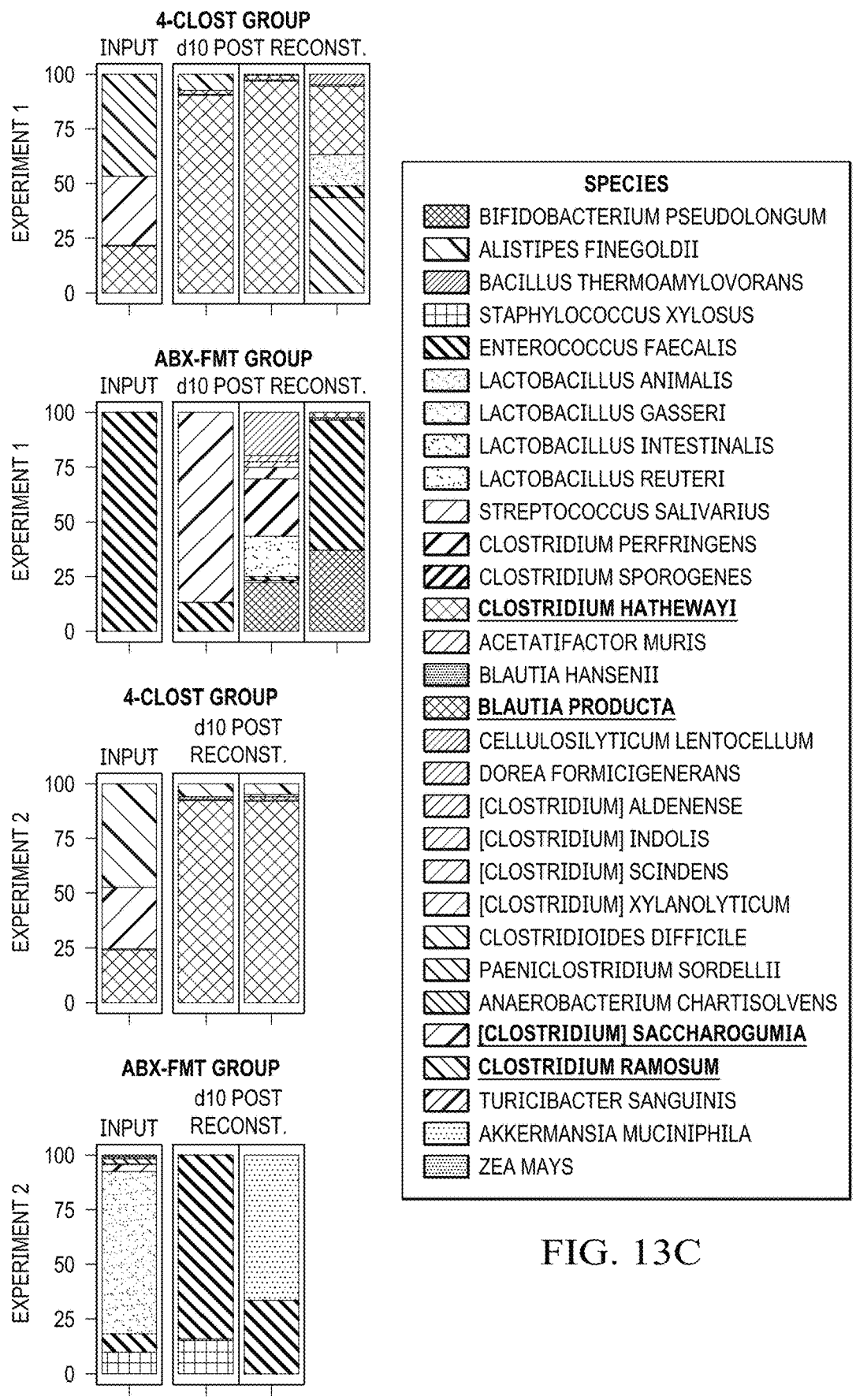
FIG. 13C is a set of graphs of 16s rRNA gene analysis showing the effects of four therapeutic bacteria in mice.

16s rRNA gene analysis of input material (gavaged bacterial cultures for 4-Clost group, fecal pellet from the antibiotic-treated donor for ABX-FMT) as well as fecal pellets from ex-GF mice 10 days post reconstitution (i.e. day of *L. monocytogenes* infection) was performed and results are presented in FIG. 13C. Columns within the d10 area represent individual mice.

Only three of the four Clostridiales used for reconstitution in the 4-Clost mixture appeared to engraft, with *C. saccharogumia* being lost in several animals by day 10 (FIG. 13C).

Overall GF mice reconstituted with a 4-Clos mixture prior to infection with L, *monocytogenes* showed virtually no intestinal *L. monocytogenes* burden or translocation to the mesenteric lymph nodes, and markedly reduced penetration into intestinal wall and visceral organs. In contrast, GF mice reconstituted with a dysbiotic microbiota were highly susceptible to *L. monocytogenes* infection, demonstrating the importance of selected commensal species in exerting *L. monocytogenes* resistance.

Various sequence accession numbers are cited herein, the contents of which are hereby incorporated by reference in their entireties. In addition, various references are cited herein, the contents of which are hereby incorporated by reference for the methods and techniques described.

The invention claimed is:

1. A method for reducing the risk of *Listeria monocytogenes* (*L. monocytogenes*) infection in a subject having a cancer, comprising administering, to the subject, a therapeutically effective amount of a composition comprising at least one of a *Clostridium saccharogumia* (*C. saccharogumia*) bacteria, a *Clostridium ramosum* (*C. ramosum*) bacteria, a *Clostridium hathewayi* (*C. hathewayi*) bacteria, and a *Blautia producta* (*B. producta*) bacteria for reducing the risk of *L. monocytogenes* infection in the subject, wherein the composition is administered before, during or after chemotherapeutic treatment of the subject.

2. The method of claim 1, wherein the composition comprises at least two of a *C. saccharogumia* bacteria, a *C. ramosum* bacteria, a *C. hathewayi* bacteria, and/or a *B. producta* bacteria.

3. The method of claim 1, wherein the composition comprises a *C. saccharogumia* bacteria, a *C. ramosum* bacteria, a *C. hathewayi* bacteria, and a *B. producta* bacteria.

4. The method of claim 1, wherein the composition comprises a *C. ramosum* bacteria, a *C. hathewayi* bacteria, and a *B. producta* bacteria.

5. The method of claim 1, further comprising reducing the risk of invasive listeriosis in the subject.

6. The method of claim 1, further comprising administering at least $10^5$ bacteria of each bacteria administered.

7. The method of claim 1, comprising administering at least one bacteria as an isolated viable bacteria or an isolated spore thereof.

8. The method of claim 1, wherein the composition is for oral, nasogastric, or rectal administration.

9. The method of claim 1, wherein the therapeutically effective amount ameliorates at least one symptom of *L. monocytogenes* infection selected from the group consisting of abdominal tenderness, abdominal pain, abdominal cramping, diarrhea, nausea, vomiting, fever, chills, fatigue, muscle aches, headache, stiff neck, back ache, confusion, loss of balance, convulsions, sepsis, meningitis, chorioamnionitis, meningo-encephalitis, and/or death, and, in pregnant subjects, placental infection, miscarriage, stillbirth, and/or premature labor.

10. The method of claim 1, wherein the therapeutically effective amount inhibits proliferation of *L. monocytogenes* in the gastrointestinal tract or the large intestine of the subject.

11. The method of claim 1, further comprising culturing a sample from the subject or detecting a *L. monocytogenes* biomarker in a sample from the subject and evaluating the *L. monocytogenes* infection in the subject.

12. The method of claim 1, wherein the composition is administered before, during, or after antibiotic treatment.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcggtaacag catttgctgc tccaacaatc                                       30

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gccattgtct tgcgcgttaa tcatttgac                                        29

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: a, c, t, g, unknown or other

<400> SEQUENCE: 3
aytgggydta aagng                                                       15

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgtcaatty htttragt                                                    18
```